(12) United States Patent
Tobinick

(10) Patent No.: US 11,612,701 B2
(45) Date of Patent: Mar. 28, 2023

(54) AUTO-INJECTOR DEVICES TO FACILITATE PERISPINAL DELIVERY OF BIOLOGICS AND DRUGS

(71) Applicant: Edward Tobinick, Boca Raton, FL (US)

(72) Inventor: Edward Tobinick, Boca Raton, FL (US)

( * ) Notice: Subject to any disclaimer, the term of this patent is extended or adjusted under 35 U.S.C. 154(b) by 201 days.

(21) Appl. No.: 16/754,866

(22) PCT Filed: Dec. 20, 2018

(86) PCT No.: PCT/US2018/066726
§ 371 (c)(1),
(2) Date: Apr. 9, 2020

(87) PCT Pub. No.: WO2019/126454
PCT Pub. Date: Jun. 27, 2019

(65) Prior Publication Data
US 2021/0196889 A1    Jul. 1, 2021

Related U.S. Application Data

(60) Provisional application No. 62/609,248, filed on Dec. 21, 2017.

(51) Int. Cl.
*A61M 5/42* (2006.01)
*A61M 5/20* (2006.01)

(52) U.S. Cl.
CPC .............. *A61M 5/427* (2013.01); *A61M 5/20* (2013.01); *A61M 2005/206* (2013.01); *A61M 2202/0007* (2013.01); *A61M 2210/1003* (2013.01)

(58) Field of Classification Search
CPC .......... A61M 5/20; A61M 5/427; A61M 5/46; A61M 2005/206; A61M 2210/1003; A61B 17/7067
See application file for complete search history.

(56) References Cited

U.S. PATENT DOCUMENTS

| | | | |
|---|---|---|---|
| 5,098,383 A * | 3/1992 | Hemmy | A61M 5/427 604/116 |
| 5,405,362 A | 4/1995 | Kramer | |
| 2004/0019326 A1 | 1/2004 | Gilbert | |
| 2006/0211982 A1 * | 9/2006 | Prestrelski | A61K 38/27 604/60 |

(Continued)

OTHER PUBLICATIONS

Novrup et al.; Central but not systemic administration of XPro1595 is therapeutic following moderate spinal cord injury in mice. J Neuroinflammation. Sep. 10, 2014;11:159. doi: 10.1186/S12 (Year: 2014).*

(Continued)

*Primary Examiner* — James D Ponton
(74) *Attorney, Agent, or Firm* — Neifeld IP Law PLLC

(57) ABSTRACT

An autoinjector device and a method of use thereof for perispinal administration, comprising: a housing with an interspinous stop; a syringe assembly slidably mounted on the housing, the syringe assembly including a needle and a fluid container, an autoinjector actuator for urging the syringe assembly with respect to the housing from a storage position to a launch position wherein the needle travels through the interspinous stop; and a cap releasably engaged to the housing.

26 Claims, 11 Drawing Sheets

(56) References Cited

U.S. PATENT DOCUMENTS

| | | | |
|---|---|---|---|
| 2009/0093830 A1 | 4/2009 | Miller | |
| 2009/0130019 A1* | 5/2009 | Tobinick | A61K 51/1051 |
| | | | 424/1.49 |
| 2010/0241102 A1* | 9/2010 | Ma | A61F 9/0017 |
| | | | 604/506 |
| 2011/0034879 A1* | 2/2011 | Crow | A61M 5/2033 |
| | | | 604/197 |
| 2014/0039658 A1* | 2/2014 | Bangera | A61B 17/3403 |
| | | | 700/98 |
| 2014/0330207 A1* | 11/2014 | McLoughlin | A61M 5/158 |
| | | | 604/198 |

OTHER PUBLICATIONS

Notification of Transmital of the International Search R$port and the Written Opinion of the In1lernational Searching Authority, or the Declaration, Form PCT/ISA/220, in agent file reference TACTOO41-4PCT, 1A application No. PCT/US18/66726, dated Mar. 17, 2019.

* cited by examiner

AUTO-INJECTOR DEVICES TO FACILITATE PERISPINAL DELIVERY OF BIOLOGICS AND DRUGS

I. FIELD OF THE INVENTION

Design, manufacture and use of autoinjector devices to facilitate perispinal delivery of biologics and drugs to mammals, including humans.

II. BACKGROUND OF THE INVENTION

The following description of the background of the invention is provided as an aid to understanding the invention and is not admitted to describe or constitute prior art. Previous patents of this inventor include U.S. Pat. Nos. 6,419,944, 6,537,549, 6,982,089, 7,214,658, 7,629,311, 8,119,127, 8,236,306, 8,349,323 and 8,900,583, all of which are hereby incorporated by reference in their entirety.

Stroke and Traumatic Brain Injury

Traumatic brain injury (TBI), a form of acquired brain injury, occurs when a sudden trauma causes damage to the brain. TBI can result when the head suddenly and violently hits an object, or when an object pierces the skull and enters brain tissue. Adverse residual neurological and brain effects from TBI occurring years before can continue. These chronic adverse effects can include difficulties with attention, concentration, planning, calculation, reading, vision, hearing, balance and motor activities such as walking or use of hands or limbs. Traumatic brain injury can occur from repeated trauma to the head, such as occurs in contact sports such as football, boxing, and soccer, or repeated concussions of any origin.

Cerebral hypoxia refers to a condition in which there is a decrease of oxygen supply to the brain even though there is adequate blood flow. Drowning, strangling, choking, suffocation, cardiac arrest, head trauma, carbon monoxide poisoning, and complications of general anesthesia can create conditions which lead to cerebral hypoxia. Symptoms of mild cerebral hypoxia include inattentiveness, poor judgment, memory loss, and a decrease in motor coordination.

Lack of adequate blood flow to the brain causes brain injury. A stroke occurs when the blood supply to part of the brain is suddenly interrupted or when a blood vessel in the brain bursts, spilling blood into the spaces surrounding brain cells. Brain cells die when they no longer receive oxygen and nutrients from the blood or there is sudden bleeding into or around the brain. There are two common forms of stroke: ischemic—blockage of a blood vessel supplying the brain, and hemorrhagic—bleeding into or around the brain. Brain injury can occur from subdural or epidural hematoma.

Brain injury can also occur due to radiation exposure or chemotherapy.

The devices and methods of the present invention are designed to treat mammals, including humans, following brain injury (BI). Causes of BI include, but are not limited to automobile accident, anesthesia accident, near-drowning, stroke, or cerebral hemorrhage. The most common causes of BI are trauma (falls, automobile accidents, or firearm accidents); stroke; birth injuries or cerebral hypoxia. BI causes widespread, unmet medical needs, producing chronic motor deficits, sensory deficits, cognitive deficits, attention deficits, and alterations in mood or behavior for which current medical treatment is inadequate.

Tumor necrosis factor (TNF) (the term "TNF" is equivalent to "TNF-alpha") is an endogenous molecule that modulates neuronal communication and the immune response. TNF plays a key role in the inflammatory response, in the immune response, and in the response to infection. TNF is formed by the cleavage of a precursor transmembrane protein, forming soluble molecules which aggregate in vivo to form trimolecular complexes. These complexes then bind to receptors found on a variety of cells. Binding produces an array of pro-inflammatory effects, including release of other inflammatory molecules, including interleukin (IL)-6, IL-8, and IL-1; release of matrix metalloproteinases; and up-regulation of the expression of endothelial adhesion molecules, further amplifying the inflammatory and immune cascade by attracting leukocytes into extravascular tissues.

Interleukins are another group of molecules that modulate the immune response. Both TNF and interleukins are cytokines. Cytokines are a group of endogenous signaling molecules. Therapeutic molecules that directly interfere with the biologic effects of cytokines (termed "cytokine antagonists", or, interchangeably "cytokine inhibitors") can be manufactured using biotechnology (e.g. recombinant DNA technology), or can be harvested from living organisms. Therapeutic molecules created by biologic processes derived from a living source are termed "biologics", in contrast to drugs that are chemically synthesized. The living sources may include humans, other animals, or microorganisms. Biologics are regulated through a specific division of the FDA. Cytokine antagonists have been developed for therapeutic human use, including biologic TNF antagonists and interleukin antagonists that take various forms, such as monoclonal antibodies, domain antibodies, antibody fragments, and fusion proteins. "TNF antagonist" and "TNF inhibitor" are terms used herein interchangeably.

Monoclonal antibodies with a high affinity for a specific cytokine will tend to reduce the biologic activity of that cytokine. Substances which reduce the biologic effect of a cytokine can be described in any of the following ways: as a cytokine blocker; as a cytokine inhibitor; or as a cytokine antagonist. In this patent, the terms "blocker", "inhibitor", and "antagonist" are used interchangeably with respect to cytokines. Domain Antibodies (dAbs) are the smallest functional binding units of antibodies, corresponding to the variable regions of either the heavy (VH) or light (VL) chains of human antibodies, and are effective cytokine antagonists. Domain antibodies are antibody fragments. Other types of antibody fragments, such as pegylated antibody fragments (e.g. certolizumab pegol) are effective cytokine antagonists.

Clemens (Clemens H J. *Die Venensysteme der menschlichen Wirbsèaule; Morphologie und funktionelle Bedeutung* (De Gruyter, Berlin, 1961) demonstrated that the internal and external vertebral venous plexuses freely intercommunicate. But Clemens did not discuss the use of the VVS to facilitate delivery of large molecules to the brain, nor did he discuss the use of the VVS for therapeutic purposes.

Groen (Groen R J, Groenewegen H J, van Alphen H A, Hoogland P V. Morphology of the human internal vertebral venous plexus: a cadaver study after intravenous Araldite CY 221 injection. *Anat Rec,* 249(2), 285-294 (1997) confirmed the fact that all three divisions of the vertebral venous system (internal and external plexuses, and the basivertebral veins) freely intercommunicated, and that all divisions of this system lacked valves. But Groen did not discuss the use of the VVS to facilitate delivery of large molecules to the brain, nor did he discuss the use of the VVS for therapeutic purposes.

Batson in 1940 (Batson O V. The Function of the Vertebral Veins and their role in the spread of metastases. *Annals of Surgery,* 112, 138-149) published information regarding the vertebral venous system. Experimentally he demonstrated a connection between the pelvic venous system and the vertebral venous system, and proposed that this was a route whereby carcinoma originating in the pelvis could metastasize to the spine. His work did not propose the use of the VVS for therapeutic purposes, nor did it discuss or imply this possibilty. His work did not disclose the methods of the present invention for delivery of biologics to the brain.

Gisolf (Gisolf J, van Lieshout J J, van Heusden K, Pott F, Stok W J, Karemaker J M. Human cerebral venous outflow pathway depends on posture and central venous pressure. *J Physiol*, 560 (Pt 1), 317-327 (2004)) recently discussed the vertebral venous system and its connections to the cranial venous system, but did not discuss the potential use of this system as a route of administration of biologics to the brain.

Groen (Groen R, du Toit D, Phillips F, et. al. Anatomical and Pathological Considerations in Percutaneous Vertebroplasty and Kyphoplasty: A reappraisal of the vertebral venous system. Spine 29(13): 1465-1471 (2004)) discussed the anatomy and function of the vertebral venous system but did not propose the use of the vertebral venous system as a route of delivery of biologics to the brain, nor did he propose the methods of the present invention.

Olmarker has filed patent applications regarding the use of anti-TNF molecules for treatment of spinal disorders, including US20010027175, 20010055594, 20030176332, 20050220791, 20010027199, and 20030039651, which have led to U.S. Pat. Nos. 6,635,250, 6,649,589, and 7,115,557 and others. None of these applications or patents discusses the perispinal use of a biologic administered superficial to the ligamentum flavum for delivery to the brain. The term "perispinal area" is defined as within 10 cm. of the spine.

In vivo distribution of radiolabeled etanercept delivered by perispinal etanercept in a mammal was investigated. Perispinal administration resulted in more selective delivery of etanercept into the cerebrospinal fluid within the cerebral ventricles than did systemic (ventral tail vein) administration. See Tobinick E., Perispinal etanercept: a new therapeutic paradigm in neurology. Expert Rev Neurother, 10(6), 985-1002 (2010).

Perispinal Administration of Etanercept

Clinical experience with perispinal administration of etanercept began with its use for spinal disorders, first reported in 2001(1-5). The therapeutic potential of etanercept for treatment of spinal disorders is today supported by independent studies, including multiple randomized clinical trials(3, 6-10). After CNS effects were noted in multiple patients treated for intractable intervertebral disc-related pain, an institutional review board-approved clinical trial of perispinal etanercept (PSE) was performed and PSE was found to produce rapid neurological improvement in patients with Alzheimer's disease(11-16). Additional clinical experience suggests the therapeutic potential of PSE for additional forms of dementia(11-19). More recently, perispinal etanercept has been successfully utilized in more than 1,000 patients for treatment of chronic intractable neurological dysfunction after stroke or brain injury(4, 20-22). The scientific rationale supporting the use of etanercept for stroke or brain injury includes multiple, independent studies and reviews(23, 24). Rapid neurological improvement, beginning within minutes of perispinal injection, is characteristically seen following PSE injection, suggesting novel patterns of etanercept distribution to the CNS after perispinal administration(24).

For treatment of brain disorders, Trendelenburg positioning for several minutes may be used immediately after PSE is administered(24).

In vivo drug distribution after perispinal administration has been investigated by independent academic scientists in collaboration with this author(16, 25, 26). In 2007, enhanced delivery of radiolabeled diethylene triamine pentaacetic acid (DTPA) into the cerebral venous system after perispinal (as compared with antecubital) injection followed by Trendelenburg positioning was observed in a human subject(16). Following this human result, in collaboration with scientists at Stanford, the in vivo distribution of radiolabeled etanercept after perispinal administration and head-down tilt in a rat was investigated(26). Positron emission tomographic (PET) imaging suggested rapid penetration of radiolabeled etanercept into the cerebrospinal fluid within the cerebral ventricles, with accentuation of signal within the choroid plexus within the ventricles(16, 26).

In 2014-2015 there were six basic science studies published providing independent evidence of the therapeutic potential of etanercept in stroke models(24). The inventor is not aware of any prior art which teaches perispinal administration of biologics using an injector device to deliver molecules to the brain, cerebrospinal fluid or the head. The present method of administration provides the patient with a better opportunity to heal, slows disease progression, and otherwise improves BI.

Perispinal administration of a molecule, when compared to systemic administration, provides one or more of the following advantages
1) greatly improved efficacy due to improved delivery of the therapeutic molecule to the brain or the cerebrospinal fluid.
2) greater efficacy due to the achievement of higher local concentration in the interspinous space, leading to improved delivery to the VVS and the brain, and cerebrospinal fluid.
3) greater efficacy due to the ability of the administered therapeutic molecule to reach the brain and cerebrospinal fluid, without degradation caused by hepatic or systemic circulation;
4) more rapid onset of action;
5) longer duration of action; and
6) potentially fewer side effects, due to lower required dosage.

Physiologic barriers which separate the brain from the blood include the so-called "blood-brain barrier" (BBB) and the "blood-cerebrospinal fluid barrier" (BCSFB). These barriers consist of a layers of cells that comprise the cerebral capillary endothelium (the BBB), and the choroid plexus epithelium (the BCSFB). These cellular barriers contain cells that are connected by tight junctions (zonulae occludens) that may be as much as 100 times tighter than junctions of other capillary endothelium. These tight junctions prevent molecules larger than about 600 daltons in molecular weight (MW) from traversing the BBB when the molecule is administered systemically i.e. by conventional subcutaneous, intramuscular, or intravenous injection at an anatomic site remote from the spine.

The vertebral venous system (VVS) is an interconnected plexus of veins which surrounds the spinal cord and extends the entire length of the spine. The spinal vertebral venous system has been termed Batson's Plexus. Because of their anatomic and functional continuity, the veins, venous sinuses, and venous plexuses of the brain and spine taken together are termed the cerebrospinal venous system (CSVS). The VVS consists of an interconnected and richly anastomosed system of veins which run along the entire length of the vertebral canal. The vertebral venous plexus, for descriptive purposes, has been separated into three intercommunicating divisions: the internal vertebral venous plexuses (anterior and posterior) lying within the spinal canal, but external to the dura; the external vertebral venous plexuses (anterior and posterior) which surround the vertebral column; and the basivertebral veins which run horizontally within the vertebrae (see accompanying FIGS. 1, 2, 2A, 3A, 3B, and 3C). Both the internal and external vertebral venous plexus course longitudinally along the entire length of the spine, from the sacrum to the cranial vault. The caval venous system and the VVS are separate and largely independent, although they are interconnected, although not in an efficient manner. Perispinal administration of a large molecule will result in efficient delivery of the large molecule to the VVS, with only a small amount of delivery of the large molecule into the caval venous system. Delivery of the same large molecule by intravenous infusion into an arm vein, for example, will deliver the large molecule to the caval venous system, expose the large molecule to dilution throughout the body, and fail to deliver the large molecule to the brain, cerebrospinal fluid, or the head as efficiently as perispinal administration.

The VVS may be used to introduce a variety of therapeutic molecules to the brain, retina, cranial nerves, and head via retrograde venous flow from the VVS into the cranial venous sinuses and the intracranial venous system. This method bypasses the well-known barrier which prevents large molecules introduced into the systemic circulation from efficiently reaching the brain (the BBB). The BBB prevents molecules larger than approximately 600 daltons from entering the brain via the systemic circulation. Virtually all biopharmaceuticals are larger than this. For example, etanercept has a molecular weight of 149,000 daltons, and insulin has a MW of 5,000 (compared with water which has a MW of 18). This method is particularly useful, therefore, for the administration of large molecules (MW larger than 600 daltons), such as etanercept, TNF monoclonal antibodies, etc., whose size when delivered systemically prevents their efficient passage into the brain, but whose potency, because of their biologic origin, is extremely high. Effective delivery of these molecules to the brain using the methods of the present invention thereby enables treatment of BI.

The vertebral venous system is both anatomically and physiologically distinct from the venous system which drains the abdomen and thorax, which has been designated by others as the intracavitary (caval) venous system, with the vertebral venous system designated as the extracavitary venous system.

Perispinal extrathecal administration is distinguished from intrathecal administration because extrathecal administration is both safer (no dural puncture, therefore no risk of CSF leak; less risk of hemorrhage; no risk of spinal cord traumatic injury; less risk of hemorrhage and infection) and is more effective at delivering the therapeutic molecule into the VVS. CSF flow from the spinal cord to the brain is slow. In contrast retrograde flow to the brain via the VVS is much more rapid.

SUMMARY OF THE INVENTION

One object of the invention is to provide an autoinjector device comprising:

a housing with an interspinous stop; a syringe assembly slidably mounted on the housing, the syringe assembly including a needle and a fluid container, an autoinjector actuator for urging the syringe assembly with respect to the housing from a storage position to a launch position wherein the needle travels through the interspinous stop; and a cap releasably engaged to the housing.

Another object of the invention is to provide a method of perispinal administration, comprising:

injecting an effective amount of a medicine into a patient in need thereof using an autoinjector device placed over an interspinous region of the patient, said device containing a housing with an interspinous stop; a syringe assembly slidably mounted on the housing, the syringe assembly including a needle and a fluid container, an autoinjector actuator for urging the syringe assembly with respect to the housing from a storage position to a launch position wherein the needle travels through the interspinous stop; and a cap releasably engaged to the housing.

Another object is to provide an autoinjector for perispinal administration of a biologic, comprising an autoinjector containing a housing with an interspinous stop.

DETAILED DESCRIPTION OF THE INVENTION

Figure 1:
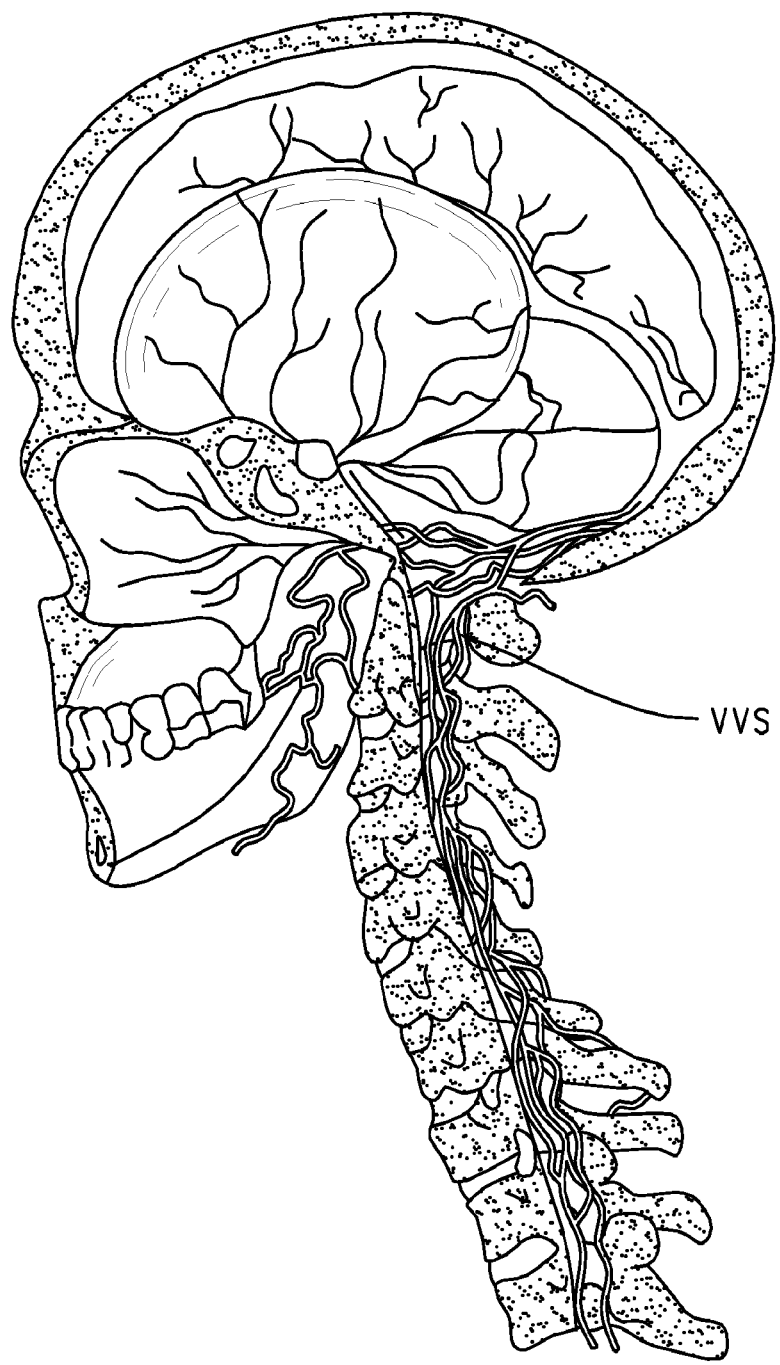
FIG. 1 is a drawing depicting a view from the side of a cross-section of the brain and the spine, showing the location and anatomic distribution of the vertebral venous system (VVS) and its continuity with the cerebral venous system.

This disclosure provides an autoinjector device that facilitates perispinal injection of drugs and biologics into the vertebral venous system. Clinical experience has shown that doctors often find it difficult to perform perispinal injections freehand using a standard syringe and needle, for reasons ranging from physical problems locating exactly where to place the needle so that it will avoid contacting bony regions of the vertebrae (e.g. spinous processes), to psychological problems relating to a fear of piercing the dural membrane or the spinal cord, to uncertainty about the proper fluid injection rate.

Some medications are routinely delivered using an autoinjector. Typical autoinjectors include a small pen-cap like cap that protects a rubber needle cover which shields the needle until it deployed through the rubber needle cover then into skin, by pressing a trigger. Exemplary autoinjectors available today include HUMIRA® Pen and Enbrel SureClick®. In general, the known autoinjectors are not suitable for perispinal delivery for several reasons, the most important being they fail to provide guidance as to where exactly to place the device for effective perispinal injection. For instance, autoinjectors typically have a large aperture which is pressed onto the skin which serves to gather the flesh into a raised target for the needle while this large aperture actually covers and hides the spot where the needle is supposed to emerge from the housing. In contrast, perispinal injection is best done directly over the back, between adjacent spinous processes, which are bones that tend to become more visible under the skin as it is stretched thinner by having the patient bend forward. Using this method one must know exactly where the needle will emerge to avoid hitting bone.

The autoinjector system disclosed herein addresses various deficiencies in the prior art by providing, in various aspects and embodiments, an improved autoinjector system which enables users to more easily administer medicine via perispinal injection. The present invention provides an autoinjector containing an interspinous stop (444) of about 1 cm in height measured from its bottom surface (where it contacts the skin) to the body of the pen through which the needle emerges upon triggering; said interspinous stop having a flat surface, or preferably a concave surface (446), to press against a spinal process of the patient, so that when the needle (105) is deployed it emerges at a defined distance from said flat, or preferably concave surface (446), ensuring that the needle enters the skin in a region between the spinous processes of two adjacent vertebrae, and a surface 445 opposing surface 446. Therefore, interspinous stop (444) serves simultaneously to 1) hold the body of the injector pen away from the skin, allowing the user to better see the target area near a chosen spinous process, while 2) providing a concave surface configured to push firmly against the chosen spinous process; so that upon triggering, 3) the needle emerges at a defined distance from the concave surface, which ensures the needle deploys into a space between adjacent vertebrae. After it emerges from the aperture (447) in the bottom surface of the interspinous stop (444) the injection needle deploys to a depth of 10-15 mm, preferably 11, 12, 13 or 14 mm.

Fluid capacity of the device may range from 1.5 to 4.0 ml, generally 1.5 to 2.5 ml, preferably about 2.0 ml. The rate of injectate delivery is from 4-10 seconds per ml, preferably 5-8 sec/ml or 10-16 seconds to inject 2 ml. For delivery into the bone marrow, however, volumes may be larger; in some embodiments for delivering cells to the bone marrow, the device fluid capacity may range up to 10 ml.

The present autoinjectors may house the medication within an enclosed housing having no mechanism for viewing the volumetric level. Optionally a transparent window may be provided in the body of the device so that a user may confirm whether or not the right medication level is present, that the color is correct, and that the solution is free of particles.

In a representative embodiment, an autoinjector is provided with a interspinous stop, a housing, a syringe assembly that is slidably mounted on the housing and having a needle and a fluid container, an autoinjector actuator for urging the syringe assembly with respect to the housing from a storage position to a launch position through said perispinal, and a cap that releasably engages with the housing and interspinous stop. According to one implementation, an autoinjector device includes a housing having distal and proximal ends, the distal end including an interfacing structure that receives a needle cap. The needle cap releasably engages with the housing. In certain embodiments, the autoinjector actuating mechanism includes a spring.

Figure 4:
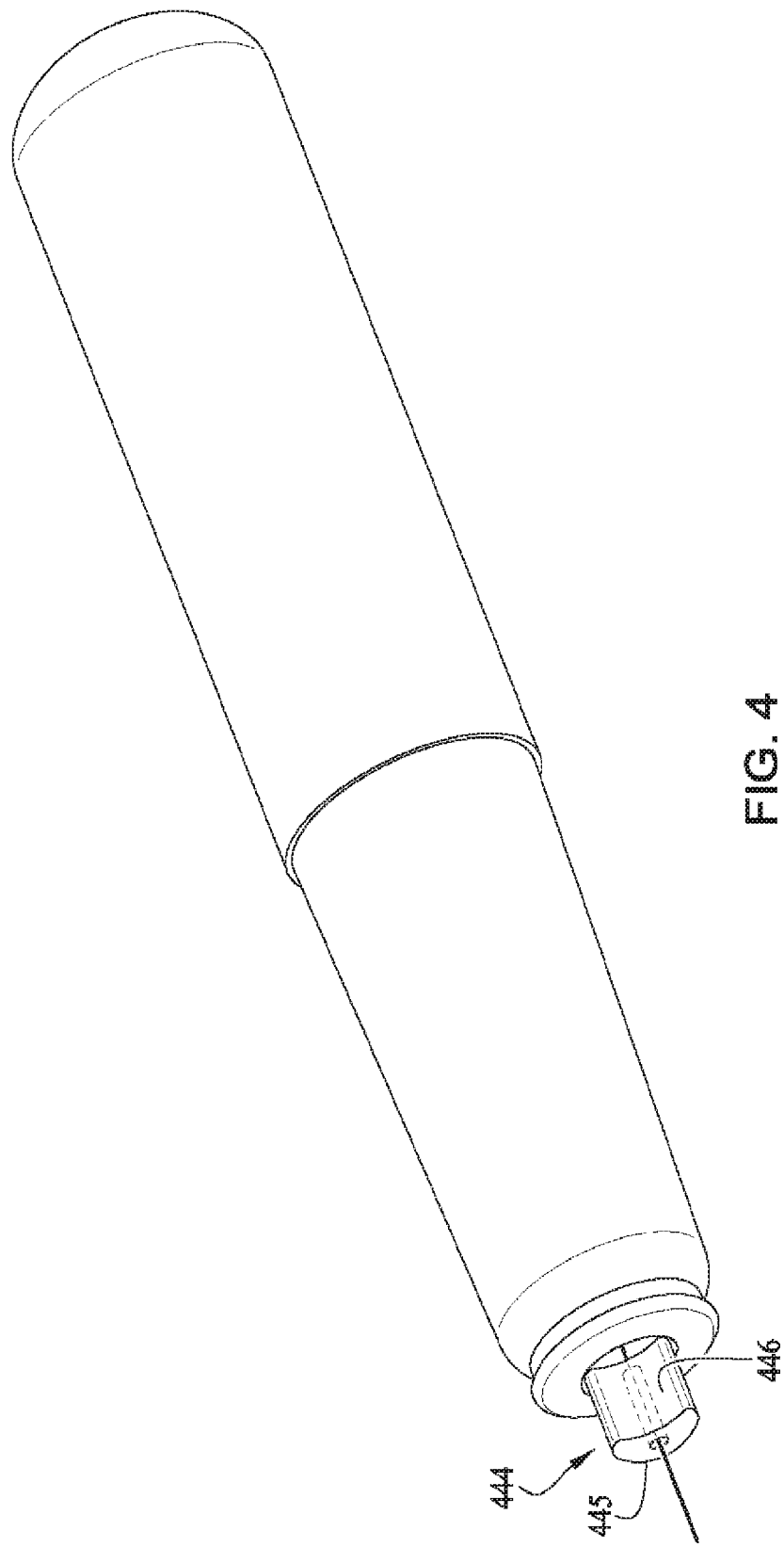
FIG. 4 shows an exemplary embodiment with a needle in the launch position.
Figure 5:
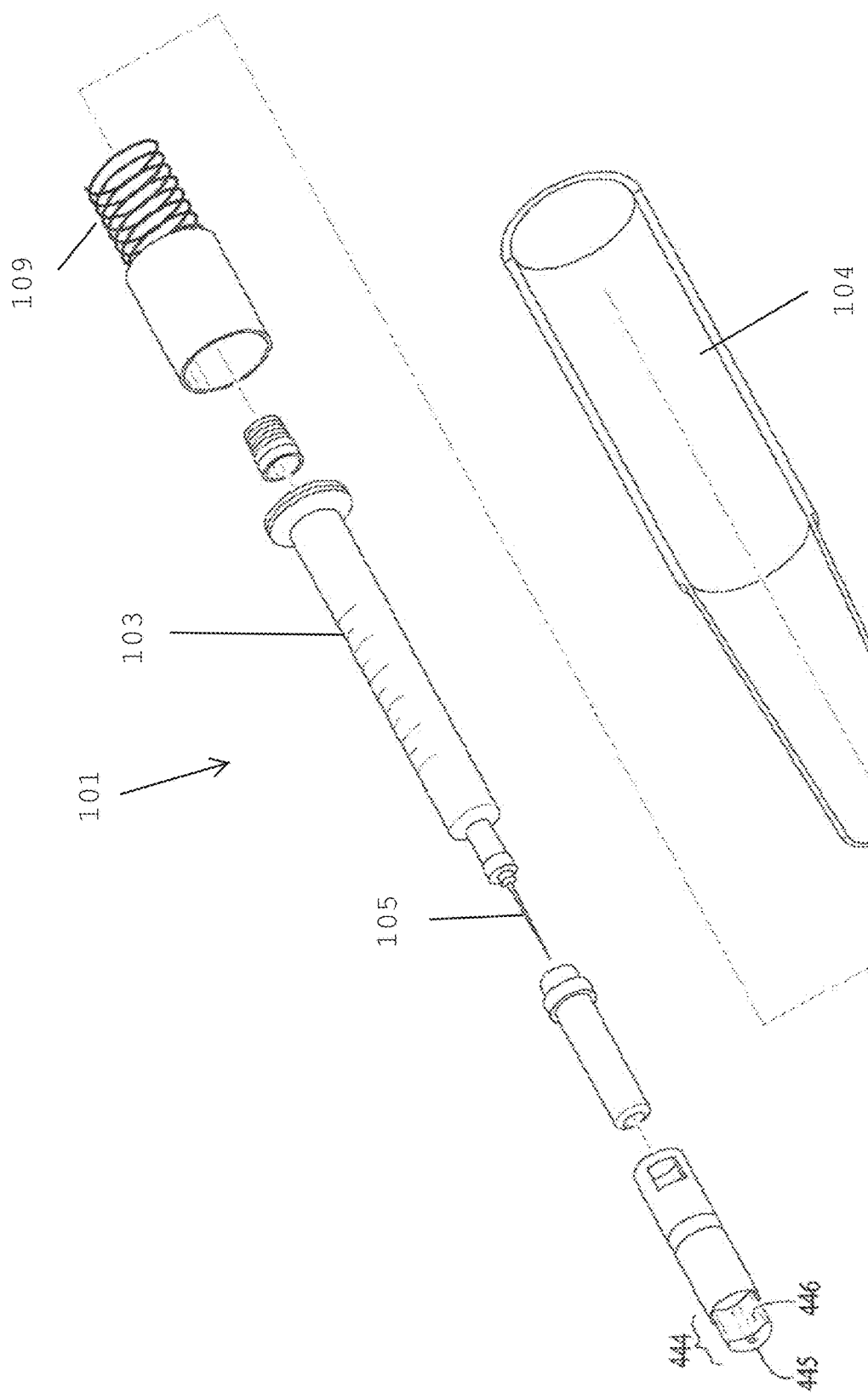
FIG. 5 depicts an exploded view of an autoinjector device of the invention.

Turning to the illustrative embodiments, FIG. 5 is an exploded view of the autoinjector system showing the housing 104 ready to receive a syringe assembly 101 that is slidably mounted within the housing 104. The syringe assembly 101 includes a needle 105 and a medication container 103. The housing 104 also includes, among other things, an actuating mechanism 109 for urging the syringe assembly 101 with respect to the housing 104 from a storage position with needle inside the needle cover to a launch position (FIG. 4) to allow automatic dispensing of the medication contained within the syringe assembly 101. As shown, the actuating mechanism 109 is spring loaded, however, any type of an energy source may be used with the device described herein. For example, a gas cylinder similar to the type used in a conventional aerosol can or the like (i.e., having a valve through which gas can be released at will and in a controlled manner) can be used. Once mated, the syringe assembly 101 is completely enclosed within the housing 104.

Figure 6:
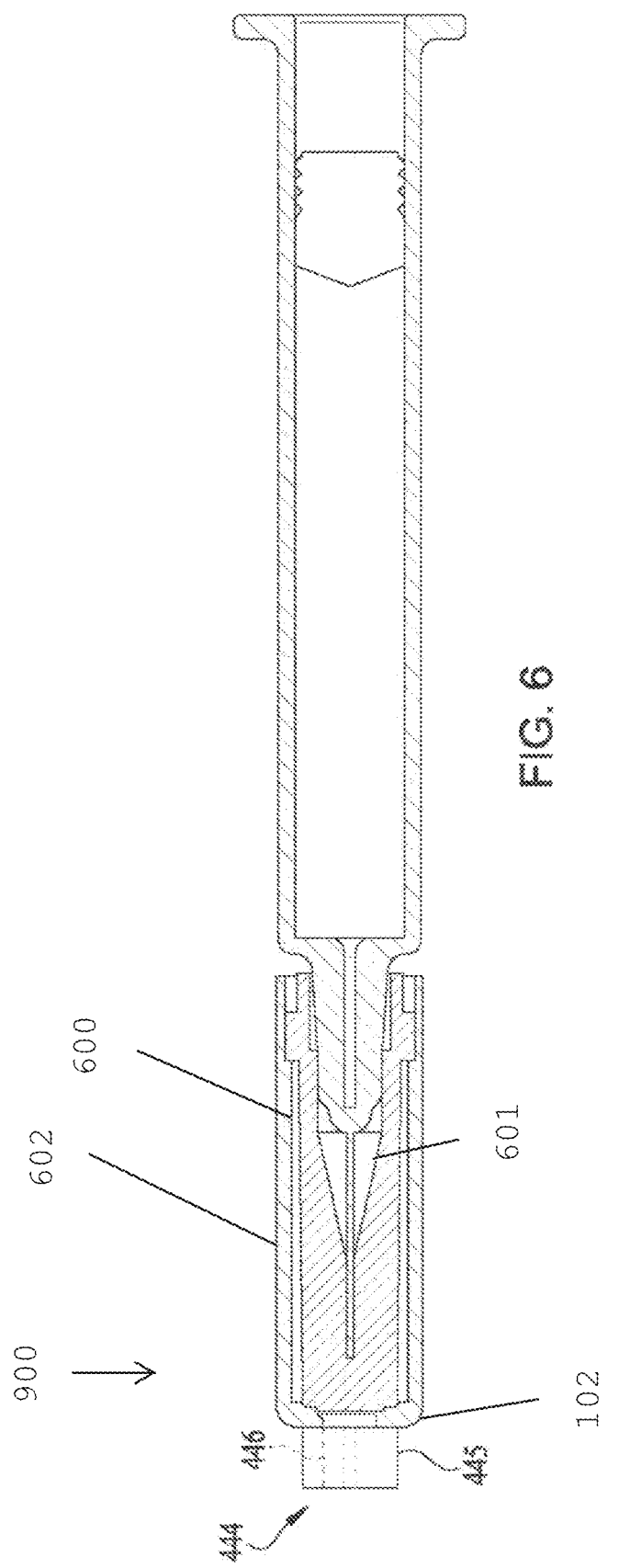
FIG. 6 depicts a longitudinal cross sectional view of an illustrative embodiment showing an interspinous stop at the end of a needle shield housing.
Figure 7:
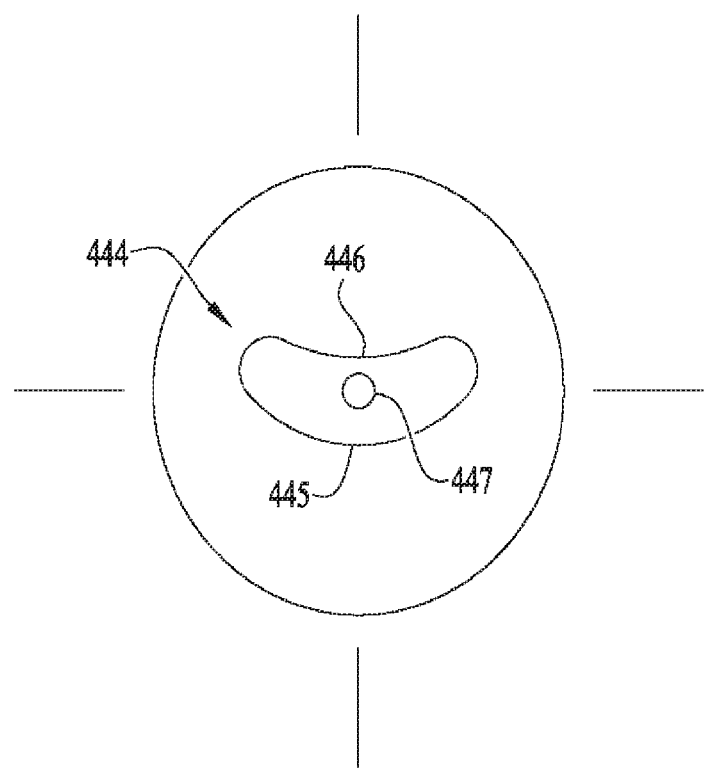
FIG. 7 shows an interspinous stop from below, with an aperture for needle deployment.
Figure 8:
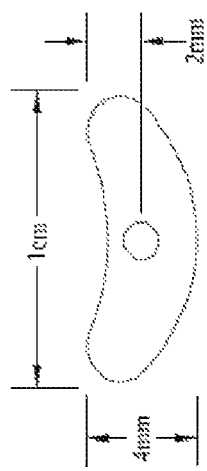
FIG. 8 shows an exemplary embodiment of an interspinous stop about four times actual size, from below, with an aperture for needle deployment.

FIG. 6 illustrates an exemplary embodiment with a rubber needle shield 601 fitted within a needle shield housing 602 and an interspinous stop 444 forming a needle cover assembly 900. A conventional hypodermic syringe assembly (for example, a syringe assembly manufactured by Becton, Dickinson and Company) may also be used with the autoinjector described herein. The needle shield housing 602 and interspinous stop 444 may be made of plastic material or other material which provides structural support for both the interspinous stop 444 and the rubber needle shield 601. The needle cover assembly 900 is fitted within the cap 102.

In certain implementations, the autoinjector system is provided to the user in a kit including the autoinjector system and an alcohol swab. In certain embodiments the autoinjector system is pre-filled with medication. In certain embodiments, the system is packaged with a pre-filled syringe that is inserted within the system prior to commercial sale. In an exemplary embodiment the pre-filled syringe includes medication to be used to treat brain injury.

In certain embodiments, the injector cap includes closed and open ends, where the cap includes a clear window disposed between the closed and open ends. The injector housing may also include a corresponding window positioned beneath the clear window of the injector cap when the cap is engaged to the housing. In certain embodiments, the cap includes longitudinal ribs extending along the length of the cap. The longitudinal ribs may be within the needle cap. The longitudinal ribs may be spaced apart so that at least one rib extends on one side of a clear window and at least one rib extends on another side of the clear window. In certain embodiments, the injector cap includes a curved interface and the housing includes a corresponding interface adapted to mate with the curved interface of the injector cap.

The medication may be for treatment of any disease or disorder in which perispinal administration is indicated, including for the treatment of brain injury, herniated disc and sciatica. In certain embodiments, the viscosity of the liquid medication is less than about 120 mPas (120 centipoise), preferably less than 100 mPas (100 centipoise) at a delivery temperature of 20° C. In certain embodiments, the viscosity of the liquid medication is between about 65 centipoise and about 120 centipoise. In certain embodiments, the viscosity of the liquid medication is between about 75 centipoise and about 100 centipoise. In certain embodiments, the viscosity of the liquid medication is higher than about 65 mPas, preferably higher than 85 mPas. In certain embodiments the viscosity of the liquid medication is about 80 centipoise.

In certain embodiments, the liquid medication is designed for refrigerated rest (e.g. at from 2-8° C.) and for injected delivery at room temperature (e.g. at or about 18-30° C.). It is to be understood that while the invention has been described in conjunction with various illustrative embodiments, the forgoing description is intended to illustrate and not limit the scope of the invention. Other aspects, advantages, and modifications are within the scope of the following claims. All documents cited herein are incorporated by reference in their entirety and made part of this application.

Perispinal Injector Devices—General Considerations, Definitions, and FDA Guidance For purposes of this invention, a "perispinal injector device" is defined as an injector device with a liquid reservoir (a syringe or cartridge) containing a therapeutic drug or biologic, that utilizes a needle, and which is specifically designed to penetrate the skin in an interspinous area directly above the backbone, to deliver a drug or biologic superficial to the ligamentum flavum, for absorption into the cerebrospinal venous system ("CSVS"). For the purposes of this invention, the term "perispinal injector device" includes autoinjectors; pen injectors; piston syringes; mechanically operated injectors; injectors with computerized or electronic elements; and syringes modified with a stabilization/targeting platform; each of which is specifically designed to accomplish perispinal delivery of a therapeutically effective amount of a drug or biologic.

The FDA in the United States has given guidance for industry regarding pen, jet, and related injectors (see *Guidance for Industry and FDA Staff Technical Considerations for Pen, Jet, and Related Injectors Intended for Use with Drugs and Biological Products*, June 2013). As this document states: "Pen, jet, and related injectors may provide an innovative approach to deliver drugs or biological products, and they may enhance safety, improve dosing accuracy, and increase patient compliance, particularly in self-administration settings." Pen, jet and related injectors may be marketed under different provisions. For example, pen injectors for general use are regulated as class II devices under 21 CFR 880.5860 (product code NSC) or 21 CFR 880.6920 (product code KZH). Jet injectors for general use, including needle or needle-free injectors, are regulated as class I devices under 21 CFR 880.5430 (product code KZE). Typically such general use injectors are regulated by CDRH. When injectors are combined with, packaged with, or labeled for use with a specific drug/biological product they may be combination products. Combination products are defined at 21 CFR 3.2(e).

Pen delivery is widely used in medicine as an alternative to syringe delivery. Pens are used for delivery of insulin, growth hormone, hepatitis C drugs, multiple sclerosis drugs, cancer drugs, biologics for treatment of autoimmune diseases, epinephrine for anaphylaxis, and migraine drugs. The advantages of pen delivery are ease of use, reduction in pain, standardization of needle length and depth of delivery, process simplification, and, in some embodiments, reduction in fear and anxiety due to hiding of the needle from the patient.

Autoinjector or pen delivery is commonly utilized for in-home subcutaneous administration by patients or caregivers of biologic TNF antagonists, including etanercept (Enbrel® single-use Prefilled SureClick® Autoinjector), golimumab (Simponi® pen) and adalimumab (Humira® pen); and interleukin antagonists, including Cosentyx®. For their FDA-approved indications (generally including diabetes mellitus, arthritides, psoriasis, or Crohn's disease), pen injectors are utilized for pen delivery into the subcutaneous regions of the thighs, upper arms or the abdomen, using needles designed for subcutaneous delivery, many in length from 4-6 mm, and patients are often instructed to pinch the skin to raise a skin fold and then inject into the skin fold.

Raising a skin fold in the perispinal area is difficult because the skin in this area, adjacent to the spinal processes, is characteristically taut and it preferably made even tauter by having the patient bend forward, so that the underlying bones are easier to locate so as to avoid hitting them with the needle. Before now perispinal injection has only been performed using standard freehand needle injection methods. The perispinal region is not suited to the use of traditional pen injectors, not only because the skin is too taut to lift a skin fold, but also because of the close proximity to the surface of the skin of the bony spinous processes and surface topography which is not flat, due to curves, humps and valleys produced by the underlying spinal processes.

In addition to human use, the methods described herein may be used to treat other mammals, including horses, dogs, and cats.

The Anatomic Problem that a Perispinal Injector Device is Designed to Address

Unlike the usual syringe, autoinjector, or pen device, a perispinal injector device is specifically designed to facilitate perispinal delivery of a drug or biologic into the cerebrospinal venous system for therapeutic (or diagnostic) purposes.

The first problem that such a device must address is the unique anatomy of the perispinal region. On the surface, the skin is this area is generally taut, so it is not suited to the production of a skin fold, the way that the skin overlying the abdomen or thigh or back of the arm is. Of even greater importance is the close proximity of the underlying bony spinous processes, which must be avoided by needles that are automatically deployed by certain autoinjectors. This is a unique anatomic problem which is not encountered in the abdominal, thigh or upper arm areas normally utilized for autoinjector, syringe or pen delivery of drugs or biologics. The soft tissue suitable for receiving a perispinal needle lies between the adjacent spinous processes in the cervical, or, in certain embodiments, the lumbar region overlying the spine.

Drug absorption into the cerebrospinal venous system is readily achieved by suitable (that is, properly designed with respect to location, volume, fluid velocity, etc.) perispinal injection in the cervical or lumbar region overlying the spine. In both of these regions, the cerebrospinal venous system has branches that lie within the interspinous space, superficial to the ligamentum flavum, so that the CSVS may be accessed by interspinous injection. Particularly in the posterior cervical region, overlying the spine in the midline, the CSVS may be accessed by a relatively superficial injection in the soft tissue underneath the skin between or superior to a cervical spinous process. Nevertheless, care must be taken to avoid needle contact with the bony spinous process. intradermal injection must also be avoided since it is not a suitable method of perispinal delivery.

Certain embodiments of the present perispinal injector devices may incorporate a stabilization/targeting platform which functions to ensure that the needle path is angled about 5-10 degrees from perpendicular to the spine to travel between adjacent bony spinous processes.

Additional Considerations Impact the Distribution of Drugs or Biologics Carried in the Cerebrospinal Venous System Volume of injectate (typically 1.5-2.5 ml, preferably 2 ml), viscosity of injectate, patient positioning after injection, and flow velocity (time of delivery, typically 5-24 seconds) of the injectate are additional considerations that impact the anatomic distribution of the injectate via the CSVS. The perispinal injector devices of this invention are designed with these anatomic considerations in mind with respect to positioning, targeting, depth and direction of needle penetration; needle length; needle diameter; volume of injectate; formulation of injectate; rate of delivery and patient positioning after injection.

Perispinal injection may be used alone, as monotherapy, or combined with other therapeutics delivered orally or otherwise, for treatment of mammals having brain, spinal, spinal cord, bone marrow, otologic, opthalmic and oncologic disorders.

Perispinal administration may be used to deliver TNF antagonists, such as etanercept, as well as other biologics to the brain and cerebrospinal fluid. These other biologics include cytokine antagonists, and growth factors which affect neuronal function, or the immune response impacting neuronal function, including, but not limited to: interleukin 1 antagonists, such as IL-1 RA (Kineret®, Amgen) and IL-1 Trap; IL-12 and IL-23 antagonists, including but not limited to ustekinumab (Stelara®); IL-17A antagonists, including but not limited to secukinumab (Cosentyx®) and ixekizumab(Taltz®); fusion proteins; BDNF; erythropoietin; GM-CSF; NGF, or other compounds with central nervous system (CNS), vascular or immune therapeutic activity. Perispinal delivery is particularly advantageous when biologics, such as etanercept, which profoundly affect neuronal function, are administered because of their efficacy at extremely low concentration (high biologic potency).

Perispinal Administration for Delivery of Therapeutic Cells to the CNS The invention provides perispinal administration of cells designed for therapeutic use in the CNS for treatment of individuals with chronic neurological dysfunction after stroke, trauma or other forms of brain injury. Cells can be delivered by perispinal administration for absorption or delivery into the cerebrospinal venous system. Therapeutic cells delivered into the cerebrospinal venous system may be used to treat a variety of brain, spinal cord, opthalmic and otologic disorders, including but not limited to acute, subacute and chronic stroke; acute, subacute and chronic brain injury (including brain injury due to trauma, hypoxia, cardiac arrest, drowning, etc.); Alzheimer's disease; frontotemporal dementia; Huntington's disease; Down's Syndrome; spinal cord injury; depression; schizophrenia; Parkinson's Disease: Amyotrophic Lateral Sclerosis; Multiple Sclerosis; CNS Lymphoma; Gliobastoma or tumors metastatic to the brain or spinal cord; macular degeneration; retinitis pigmentosa; glaucoma; sensorineural hearing loss; or Meniere's Disease.

Perispinal administration of cells designed for therapeutic use is an innovative treatment method. Currently therapeutic cells have successfully been utilized for treatment of chronic stroke (SB623 mesenchymal stem cells surgically transplanted into the perilesional brain through neurosurgical burr holes and needle delivery through the brain parenchyma (Steinberg G K, Kondziolka D, Wechsler L R, Lunsford L D, Coburn M L, Billigen J B, et al. Clinical Outcomes of Transplanted Modified Bone Marrow-Derived Mesenchymal Stem Cells in Stroke: A Phase 1/2a Study. Stroke. 2016 July; 47(7):1817-24). Clinical trials of these same SB623 (SanBio Ltd.) stem cells for treatment of chronic motor dysfunction after traumatic brain injury are ongoing. Perispinal administration of SB623 cells enables the delivery of these same stem cells to the brain and/or the spinal cord via the cerebrospinal venous system without the necessity of neurosurgery, thereby avoiding surgical morbidity and potential adverse consequences of general anesthesia.

Perispinal administration of therapeutic cells, including but not limited to SB623 cells, can be performed using a syringe or using the perispinal injector devices of the present invention. Both of these alternative delivery methods are methods of the present invention. Perispinal administration of SB623 cells can be successfully performed using the number and volume of SB623 cells described in Steinberg G K, Kondziolka D, Wechsler L R, Lunsford L D, Coburn M L, Billigen J B, et al. Clinical Outcomes of Transplanted Modified Bone Marrow-Derived Mesenchymal Stem Cells in Stroke: A Phase 1/2a Study. Stroke. 2016 July; 47(7): 1817-24; alternatively, larger or smaller volumes or amounts of cells are delivered if within one order of magnitude larger or smaller than the quantities specified therein. Perispinal administration of therapeutic cells can be used to deliver stem cells, neural stem cells, bone-marrow derived stem cells, mesenchymal stem cells, autologous stem cells, SB618 stem cells (SanBio Ltd.), cytotoxic t-cells, or other types of cells.

One group of embodiments of the present invention include the perispinal administration of SB623 cells superficial to the ligamentum flavum in the posterior cervical area overlying the spine at the C7-71 interspace for absorption into the cerebrospinal venous system, using a dose within the range of 250,000 to 2.5 million cells in aqueous or saline suspension in a total volume ranging from 1.5 to 3.5 ml. at a concentration within the range of 10 to 1,000 cells per microliter injected at a rate within the range of 4 to 10 seconds per ml. using a perispinal injector device or a syringe fitted with a 27 gauge needle, followed by 5 minutes of head-down Trendelenburg positioning to treat a patient with chronic post-stroke neurological dysfunction or chronic neurological dysfunction after other forms of brain injury, including, but not limited to, traumatic brain injury. A latitude of modification, change, and substitution is intended in the foregoing disclosure, and in some instances, some features of the invention will be employed without a corresponding use of other features.

This invention also includes perispinal injector device delivery of cellular therapeutics into the perispinal area superficial to the ligamentum flavum for absorption into the cerebrospinal venous system, including perispinal injector device delivery of neural and/or mesenchymal stem cells, for treatment of other forms of CNS injury; for treatment of neurodegenerative disorders (including Alzheimer's disease; Parkinson's disease; Huntington's disease; Amyotrophic Lateral Sclerosis, Frontotemporal dementia, etc.); and for treatment of spinal cord injury. In one such embodiment perispinal administration of SB623 cells superficial to the ligamentum flavum is performed overlying the spine in the posterior cervical, thoracic, or lumbar region area for absorption into the cerebrospinal venous system and delivery to the spinal cord or the perispinal region adjacent to the spinal cord, using a dose within the range of 250,000 to 2.5 million cells in aqueous or saline suspension in a total volume ranging from 1.5 to 3.5 ml. at a concentration within the range of 10 to 1,000 cells per microliter injected at a rate within the range of 4 to 10 seconds per ml. using a perispinal injector device or a syringe fitted with a 27 gauge needle, to treat a patient with spinal cord injury or chronic spinal pain, including but not limited to sciatica, cervical radiculopathy, lumbar radiculopathy, chronic low back pain, or spinal stenosis. A latitude of modification, change, and substitution is intended in the foregoing disclosure, and in some instances, some features of the invention will be employed without a corresponding use of other features.

This invention also includes perispinal injector device delivery of cellular therapeutics into the perispinal area superficial to the ligamentum flavum for absorption into the cerebrospinal venous system and delivery of cells to the bone marrow, for treatment of oncologic or hematologic disorders, including perispinal injector device delivery of hematopoietic cells, bone marrow cells, or stem cells.

Localized administration of drugs and biologics for the treatment of brain disorders has many clinical advantages over the use of conventional systemic treatment. Local administration of a biologic results in its diffusion through local capillary, venous, arterial, and lymphatic action to reach the therapeutic target. In addition local administration of a large molecule in the vicinity of the spine (perispinal administration) without direct intrathecal injection has the key advantage of improved delivery of the molecule to the brain via the cerebrospinal fluid (CSF), thereby bypassing the blood-brain barrier (BBB). Delivery into the CSF is enhanced by transport via the CSVS. Intrathecal injection also delivers the molecule into the CSF, but carries with it the disadvantages of possible infection, hemorrhage, and CSF leak through a tear in the dura.

The term "treatment" as used herein in the context of treating a condition, refers generally to the treatment and therapy, whether a human or an animal, in which some desired therapeutic effect is achieved, for example the inhibition of the progression of the condition or illness, and includes the reduction in the rate of progress, a halt in the progression of an illness, amelioration of the adverse condition, and cure of the condition. Treatment as a prophylactic measure, as well as combination treatments and therapies are also included.

As used herein, "therapeutically effective" refers to the material or amount of material which is effective to prevent, alleviate, or ameliorate one or more symptoms or signs of a disease or medical condition, produce clinical improvement, delay clinical deterioration, and/or prolong survival of the subject being treated.

As used herein, "subject" refers to animals, including mammals, such as human beings, domesticated animals, and animals of commercial value.

As used herein, "an initial dose containing an effective amount" of therapeutic means that the subject was not treated with that therapeutic before.

Figure 2:
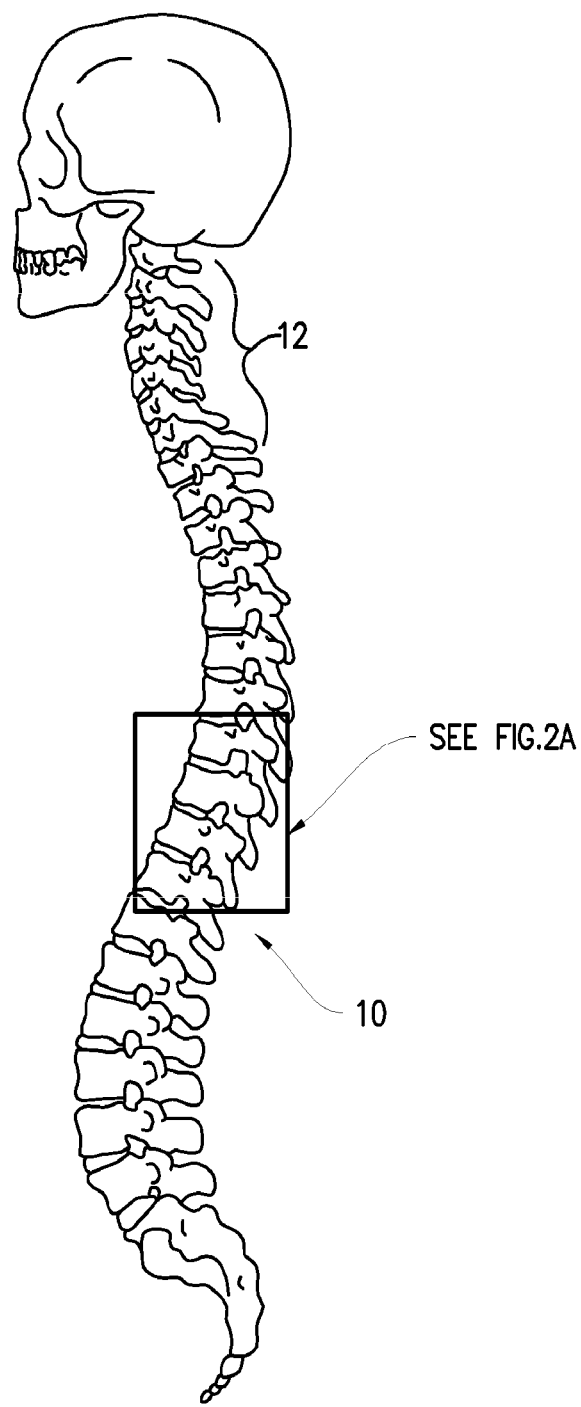
FIG. 2 is a drawing depicting a view from the side of a cross-section of the skull and the spine of a human.
Figure 2A:
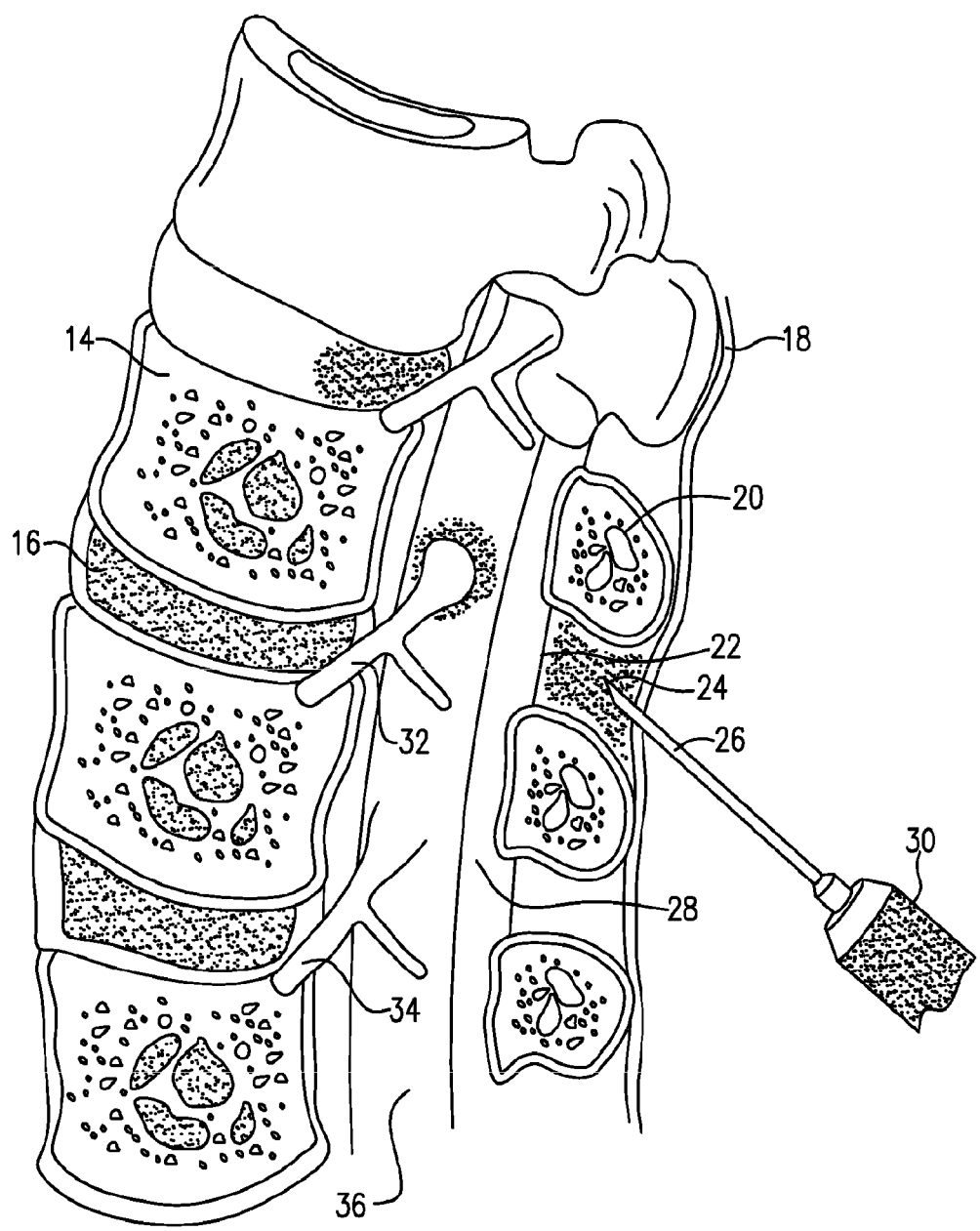
FIG. 2A is a diagram depicting perispinal administration to a humanA, in accordance with the present invention.
Figure 3A:
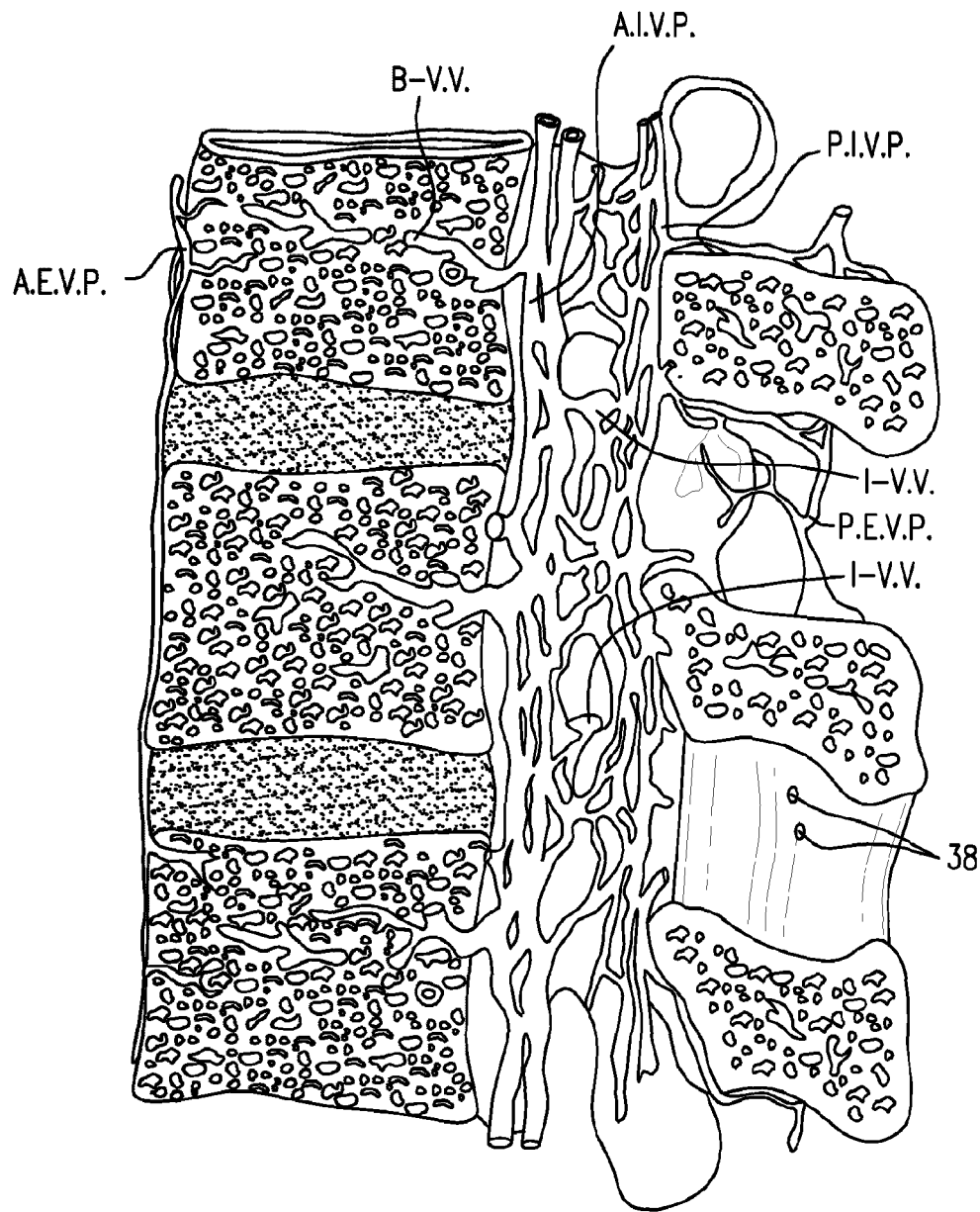
FIG. 3A is an enlarged elevational cross sectional view of the spinal area and the vertebral venous system (VVS) and its anatomic relationship to the interspinous space and other anatomic elements of the spine.
Figure 3B:
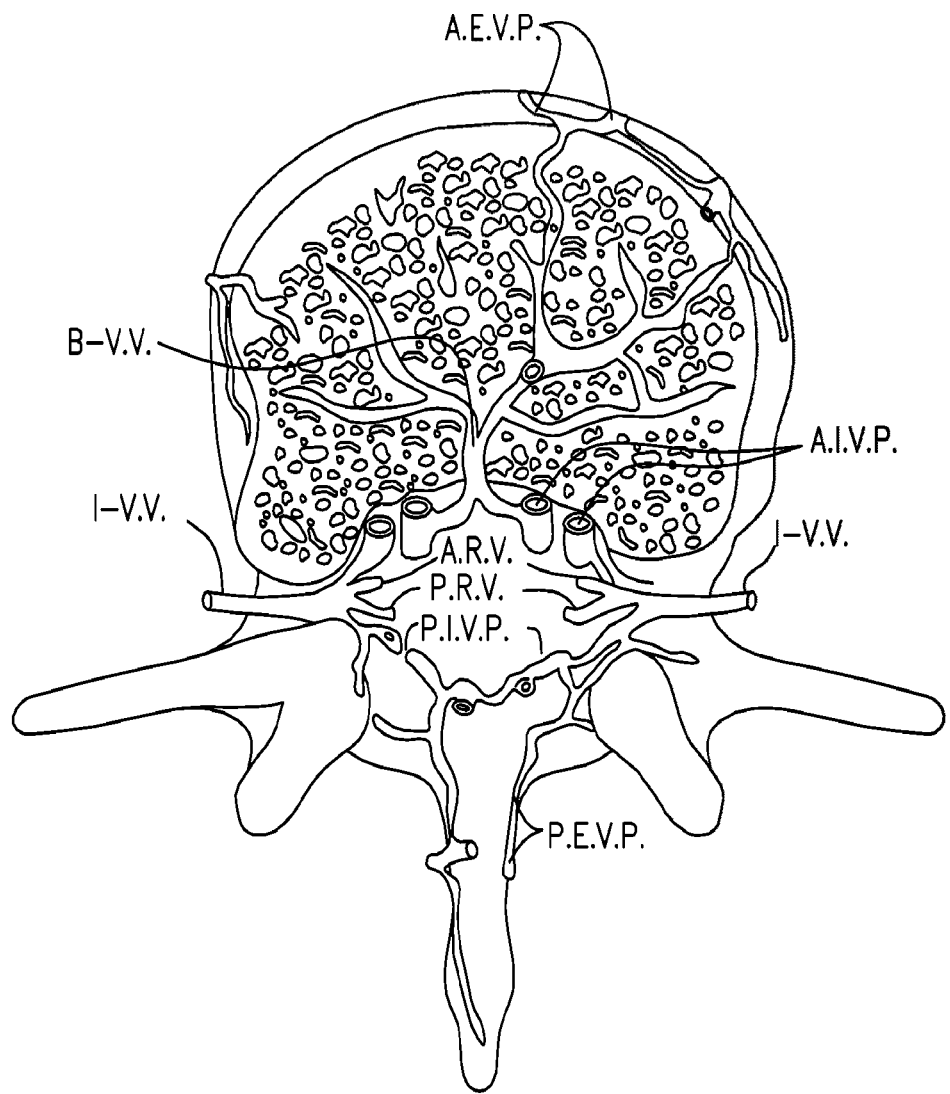
FIG. 3B is an enlarged horizontal cross sectional view of the spinal area and the vertebral venous system and its anatomic relationship to the interspinous space and other anatomic elements of the spine.
Figure 3C:
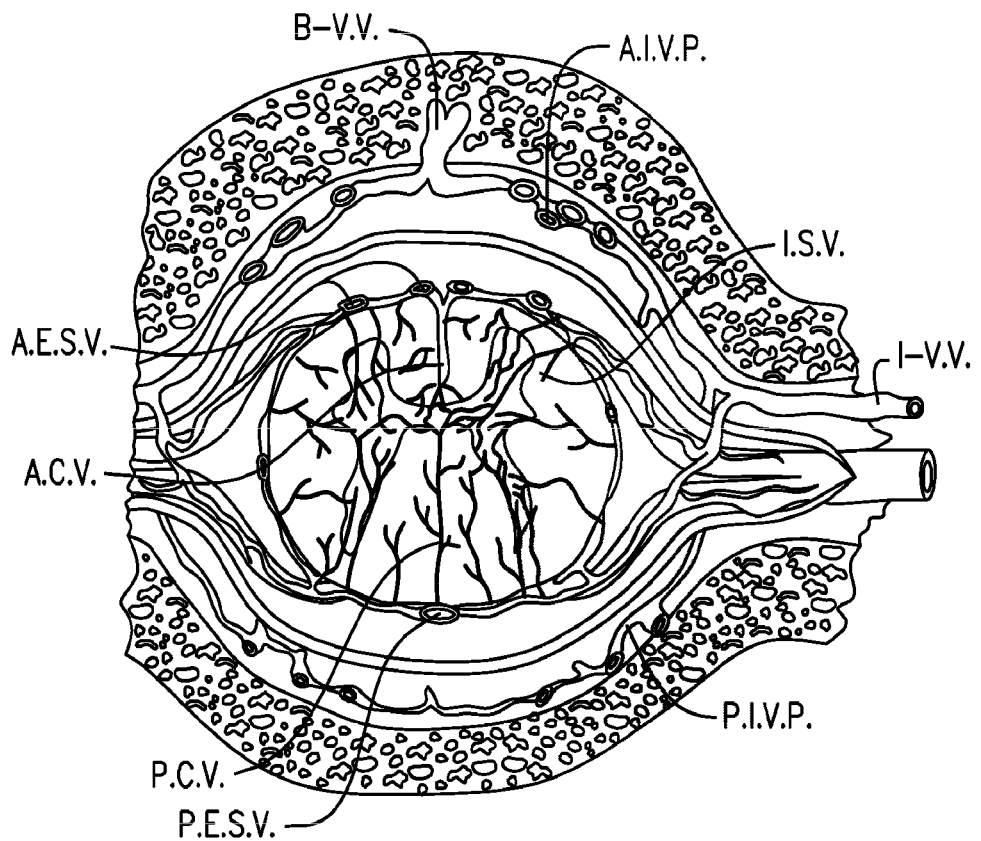
FIG. 3C is an enlarged horizontal cross sectional view of the spinal area and the VVS and its anatomic relationship to the interspinous space and other anatomic elements of the spine.

Abbreviations for FIGS. 3A, 3B, and 3C:
A.C.V.—Anterior Central Vein
A.E.S.V.—Anterior External Spinal Veins
A.E.V.P.—Anterior Externol Vertebral Plexus
A.I.V.P.—Anterior Internal Vertebral Plexus
A.R.V.—Anterior Radicular Vein
B-V.V.—Basivertebral Vein
I.S.V.—Internal Spinal Veins
I-V.V.—Intervertebral Vein
P.C.V.—Posterior Centrol Vein
P.E.S.V.—Posterior External Spinal Vein
P.E.V.P.—Posterior External Vertebral Plexus
P.I.V.P.—Posterior Internal Vertebral Plexus
P.R.V.—Posterior Radicular Vein FIG. 1 depicts the anastomoses between the cranial and vertebral venous systems. Perispinal administration for delivery to the brain and other structures of the head is preferably performed by a percutaneous injection into an interspinous space, or into the anatomic area superficial to the interspinous space (superficial to the interspinous ligament and deep to the skin) in the posterior cervical area (12 in FIG. 2). As shown in more detail in FIG. 2A, hollow needle (26) containing etanercept (or other therapeutic molecule of this invention) in solution (30) is injected through the skin 18 into the interspinous space 24. If the needle were carried further it could penetrate the ligamentum flavum (22), delivering the therapeutic molecule into the epidural space (28) surrounding the spinal cord (36), although in this invention the ligamentum flavum is not penetrated by the needle, and the therapeutic molecule is deposited into the interspinous space more superficially, without penetration of the ligamentum flavum. The therapeutic molecule in the interspinous space drains into the vertebral venous system, and is then carried to the brain and other structures of the head. (34) is a spinal nerve root.

The interspinous space (24) is defined as the space between two adjacent spinous processes (20). FIG. 3A shows the interspinous space (24) having veins (38) (FIG. 3A) which collect the therapeutic molecule, e.g. etanercept, which reaches the interspinous space after percutaneous interspinous injection and which veins drain said therapeutic molecule into the VVS, so that, utilizing the physical maneuvers of the present invention, the therapeutic molecule is transported via retrograde venous flow into the intracranial veins via the anastomoses depicted in FIG. 1, and thence to the brain or other structures of the head.

A venous system is routinely conceptualized as a system that drains blood from a target area or organ. For example, the venous system which drains the kidneys is widely acknowledged to be a vascular system that drains blood from the kidneys, not as a way of delivering a therapeutic molecule to the kidneys. Likewise the venous system of the brain is widely recognized as a system which functions to drain blood from the brain. It is counter-intuitive to use the CSVS to deliver a therapeutic molecule to the brain, by conventional thinking, which is that this venous system functions to drain venous blood away from these anatomic sites. Therefore the apparatus described here is in this way counter-intuitive, because it relies on the vertebral venous system to deliver therapeutic molecules (including specifically large molecules) to the brain, cerebrospinal fluid, or the head. This delivery is accomplished by retrograde venous flow (opposite from the usual direction), which is made possible by the lack of valves in this venous system, and by the proper use of gravity and positioning of the patient so that venous flow in the desired direction is accomplished. The rich connections between the cranial venous system and the vertebral venous system were beautifully depicted by Breschet (Breschet G. *Recherches anatomiques physiologiques et pathologiques sur le systáeme veineux* (Rouen fráeres, Paris, 1829), but this anatomic route still remains largely unrecognized by the medical community.

Indications for Perispinal Injector Device Delivery

Perispinal injection (by perispinal pen, autoinjector or syringe) represents a novel emerging method of drug delivery to the central nervous system (CNS), spine, bone marrow, inner ear or retina. Physiological barriers prevent all large molecules from efficiently penetrating into the CNS after systemic administration. Perispinal injection is designed to take advantage of the valveless, bidirectional venous flow within the cerebrospinal venous system to enhance delivery of drugs to the CNS, spine, bone marrow, inner ear or retina. Perispinal injection delivers a drug into the anatomic area posterior to the ligamentum flavum, an anatomic region drained by the external vertebral venous plexus, a division of the cerebrospinal venous system. Blood within the external vertebral venous plexus communicates with the deeper venous plexuses of the cerebrospinal venous system, including the cerebral venous sinuses, bone marrow and spinal cord. See the inventor's publication, Tobinick E L. *Perispinal Delivery of CNS Drugs*. CNS Drugs. 2016; 30(6):469-80, which is incorporated by reference in its entirety.

Perispinal Injector Device Delivery is specifically designed to deliver a therapeutic dose of a drug or biologic into the perispinal area for treatment of any of the following disorders:

Brain Disorders, including but not limited to Stroke; Chronic Stroke; Subarachnoid Hemorrhage; Intraparenchymal Hemorrhage; Intraventricular Hemorrhage; Traumatic Brain Injury; Anoxic Brain Injury; Cerebral Palsy; Spasticity; Neurodegenerative diseases, including but not limited to Alzheimer's Disease; Parkinson's disease; Frontotemporal Dementia; Non-Alzheimer Dementias; Amyotrophic Lateral Sclerosis; Multiple Sclerosis.

Spinal and Spinal Cord Disorders, including but not limited to: Spinal Pain; Sciatica; Cervical Radiculopathy; Fibromyalgia; Chronic Spinal Pain; Spinal Cord Injury; Ankylosing Spondylitis; Psoriatic Arthritis; Rheumatoid Arthritis.

Bone Marrow Disorders, including but not limited to leukemia, oncological disorders, hematologic disorders, and spinal metastases.

Otologic Disorders, including but not limited to hearing loss and tinnitus.

Opthalmic Disorders, including but not limited to visual loss; retinal disorders, including macular degeneration and retinitis pigmentosa.

The present invention, in some embodiments, utilizes a new type of autoinjector or pen that is specifically designed for perispinal injection. Previously, perispinal delivery has been accomplished by syringe delivery. Etanercept has been delivered perispinally by this inventor for more than 15 years, exclusively by syringe delivery. The perispinal injector devices of this invention are designed to facilitate perispinal delivery so that perispinal injector device delivery can be effectively and safely accomplished and utilized for professional use by primary care physicians and physicians of all specialties initially and then, eventually, by nurses, ancillary medical personnel, and finally for personal use by patients and their caregivers.

The bony spinous processes, in the cervical region in particular, make the use of the typical pen or autoinjector impractical and potentially hazardous and also potentially ineffective because the presence of bone adjacent to the surface of the skin is a hazard. One does not want the injector needle to contact the bone since needle contact with bone could prevent delivery of the liquid injectate to the patient.

The purpose of present perispinal injector devices is to deliver the medicine being injected into the anatomic area drained by the cerebrospinal venous system. The preferred area for delivery is the anatomic region below the surface of the skin, superficial to the ligamentum flavum and between the adjacent spinal processes. This region includes both the deeper interspinous space, the more superficial interspinous space and the subcutaneous region in the midline posterior to the spine, all of which is generally within 10 cm. of the spine. The present invention includes perispinal injector devices that are uniquely designed to facilitate safe and efficient perispinal delivery of a drug or biologic into the catchment area of the cerebrospinal venous system posterior to the spine so as to enable non-invasive delivery of a therapeutically effective dose of the drug or biologic to the brain, cerebrospinal fluid, spine, bone marrow or spinal cord, without the necessity of needle delivery through the ligamentum flavum.

The perispinal pen or autoinjector of the invention contains a liquid reservoir that holds a volume of injectate ranging from 1.5-4 ml. Most embodiments contain a fixed dose, although in certain embodiments the delivered dose may be varied by utilizing a dose-setting mechanism, such as a dial, to set the desired dose. The fluid path is directly from the reservoir into the needle, then through the skin into the subcutaneous space that is immediately underneath the designated skin target area and thence into the cerebrospinal venous system. The pen may contain a spring loaded or piston mechanism to facilitate reliable needle delivery and a reliable actuation device, usually a thumb button.

After needle insertion and upon completion of the injection in some embodiments the needle may automatically withdraw to within the cylindrical sheath that protects and hides the needle. In some embodiments needle delivery is automated and spring-activated; in others, needle insertion may be performed manually. Some embodiments utilize pre-attached needles; in others the needle may be manually attached.

In many embodiments the perispinal pen is a disposable autoinjector that utilizes a single-use, pre-filled syringe to deliver a monodose formulation where the dose is fixed and fully injected. In some embodiments, the drug may be lyophilized and delivered using a dual-chamber cartridge to inject the full dose after reconstitution. Embodiments of the perispinal pen may include any or all of the following features:

A stabilization/targeting platform to facilitate correct positioning of the device over a suitable interspinous space Translucent or clear viewing window to enable visualization of particulate matter or discoloration of the syringe contents before injection Interlock or other safety mechanism to prevent inadvertent actuation Audible and/or tactile start and end of injection operator feedback Needle retraction or shielding to reduce inadvertent needlestick injury An "interspinous stop" element used to help position the device over a suitable interspinous space (more fully explained below)

In some embodiments of the invention the interspinous stop 444 is a plastic, rubber or other soft, moldable material that will generally hold its shape. The interspinous stop touches the skin surface and is used to help define a safe static position for the perispinal injection device in relation to the caudal or cranial distance from an adjacent underlying spinous process. In some embodiments the interspinous stop is placed cranial to the needle; in others it is placed caudal.

Prior to injection the skin target area, in the posterior midline overlying the spine, is selected to correspond to the skin area between two adjacent spinous processes, and may be so marked, with intersecting vertical and horizontal skin marking lines, followed by skin disinfection. The autoinjector is then positioned immediately on top of this skin target area with, e.g., concave surface 446 against a spinous process, and visualized to confirm that the needle targeting sheath is directly overlying the skin target area.

The pen injector can then be activated once at a 90-80 degree angle with the skin is confirmed, preferably 85-80 degrees, i.e. the angle is inclined slightly in the cranial direction. The pen is held securely for the duration of the injection and then removed.

The advantages of pen and/or autoinjector delivery are ease of use, reduction in pain, standardization of needle length and depth of delivery, reduction in pain and reduction in anxiety due to process simplification and hiding of the needle to the observer. Other advantages include facilitating the use of perispinal delivery of drugs and biologics by primary care physicians, all medical specialists, ancillary medical personnel and personal use by caregivers by:
1. Simplification and standardization of the perispinal injection procedure;
2. Increased accuracy of the perispinal injection procedure;
3. Increased efficiency and efficacy of the perispinal injection procedure;
4. More accurate targeting of the skin area overlying the interspinous space;
5. Reduced pain and discomfort of the perispinal injection procedure;
6. Improved safety of the perispinal injection procedure both for the patient and the operator (less risk of needle stick).

An object of the invention is to provide large molecules delivered via the vertebral venous system using a perispinal injection device for suppression and inhibition of specific cytokines in a human to improve neurological function following BI.

Another object is to administer a biologic into the perispinal area, using a perispinal injection device, to deliver said biologic via the CSVS, to improve neurological function following BI.

Another object is to provide a biologic using a perispinal injection device delivered via the vertebral venous system so that it is delivered to the brain, retina, cranial nerves, bone marrow or auditory apparatus in a therapeutically effective dose and thereby improve neurological function following BI.

Another object is to provide large molecules, delivered using a perispinal injection device, that produce biologic effects by inhibiting the inflammatory cascade in the human body for the immediate, short term (acute conditions) and long term (chronic conditions), such that these biologic effects will produce clinical improvement in the patient and will give the patient a better opportunity to heal or otherwise improve neurological function following BI.

Another object is to provide novel and improved routes of administration using a perispinal injection device for the selected TNF antagonist so that it enters the CSVS in a therapeutically effective amount for the treatment of a human following BI such that the use of this antagonist with this method results in delay of disease progression in a manner that is both safe, effective, and economical.

Another object is to provide novel and improved routes of administration using a perispinal injection device for the selected biologic so that it enters the CSVS in a therapeutically effective amount for the treatment of a human following BI such that the use of this biologic with this method results in improved health in a manner that is both safe, effective, and economical.

Another object of the present invention is to provide a method to deliver etanercept across the blood-brain barrier using a perispinal injection device so that it is delivered to the brain in a therapeutically effective dose and thereby improve neurological function following BI.

Another object is to provide a biologic administered through the perispinal route using a perispinal injection device as a new method of use of such molecules so that the use of these molecules will improve neurological function following BI.

Another object is to provide a method to deliver an anti-TNF biologic so that it is delivered to the brain or the cerebrospinal fluid using a perispinal injection device in a therapeutically effective dose and thereby improve neurological function following BI.

Another object is to provide inhibitors of p38 MAP kinase, inhibitors of spleen tyrosine kinase, inhibitors of Jak3 kinase, and interleukin inhibitors, using a perispinal injection device, for treatment of a mammal following BI.

Preferred embodiments include, but are not limited to one of more of the following features:
1. Volume of injectate: 1.5 to 4 ml. This volume distinguishes the perispinal injector device from the injector devices designed for the FDA-approved systemic subcutaneous applications (such as psoriasis or rheumatoid arthritis), in which lower volumes (usually 0.5 to 1.0 ml) are preferred.
2. Viscosity of injectate: Viscosity approximating that of plain water at body temperature is preferred.
3. Patient positioning after injection: For treatment of brain, opthalmic or otologic disorders, Trendelenburg positioning immediately after perispinal delivery is preferred. Trendelenburg positioning is not necessary for bone marrow and spinal applications.
4. Velocity (flow of delivery): Rate of injectate delivery is between 4-10 seconds per cc, preferably 4-8 sec/cc or 8-16 seconds to inject 2 ml.
5. Needle type: Sharp beveled needles are preferred. Lubricated needles to ease the discomfort of injection are also preferred but are optional. Needle gauge 27-30 are preferred.
6. Needle length: 6 mm to 25 mm beyond the bottom surface of the interspinus stop is preferred. One preferred length is 10 mm.
7. Biologic: For treatment of chronic neurological dysfunction after stroke or traumatic brain injury, the use of etanercept or etanercept biosimilars, including but not limited to SB4 (Samsung Bioepsis), brand name Benepali® or Brenzys®; GP2015 (Sandoz), brand name Erelzi®; Davictrel (HD203) (Hanwha Chemical); CHS-0214 (Coherus Biosciences), Etacept (Cipla); Intacept (Intas); Etanar/Yisaipu (Shanghai CP Guojian Pharmaceutical), etc., is a preferred embodiment, at a dose ranging from 5 mg to 50 mg. Preferred embodiments include, but are not limited to, pre-filled monodose autoinjectors loaded with an etanercept dose ranging from 10 mg to 50 mg, in a volume of sterile water (volume 1.5-4 ml) for perispinal delivery overlying the cervical spine (C4-T1) in the posterior midline of the human body, at a depth of needle insertion ranging from 6-28 mm.; using a needle of gauge 27-30; and rate of delivery 4-15 seconds per ml.

The insult to the brain from each of the mechanisms enumerated (including hypoxia, acute deprivation of blood flow, radiation, chemotherapy and trauma, etc.) produces an inflammatory response that results in chronic glial activation and chronic overproduction of inflammatory cytokines, including TNF. These consequences of brain injury may result in chronic neurological deficits. For the purposes of this patent neurological deficits lasting three months or longer after the acute brain injury (trauma, stroke, etc.) are considered chronic, and are defined as "chronic brain injury". Chronic brain injury includes "chronic stroke", "chronic traumatic brain injury", etc. Chronic brain injury includes patients who are comatose or semi-comatose.

This application concerns the use of biologics for treatment of humans and other mammals following brain injury (BI), including treatment of chronic brain injury. The methods of the current invention using a perispinal injection device may successfully treat mammals that have suffered brain injury in the remote past i.e. 3-11 months or 1-2, 3, 4, 5 and even 10 years after the acute event. Preferred embodiments of the present invention include treatment of a human or other mammal long after initial healing from the acute event, such as more than three months or more than six months or more than one year or more than eighteen months or more than two years after the acute event. The methods of the present invention may also be used to treat sub-acute brain injury in the time period of two weeks to three months after the acute event. Sub-acute brain injury includes patients who are comatose or semi-comatose. The methods of the present invention may also be used to treat acute stroke or brain injury, i.e. within minutes, hours, or days of the acute stroke or brain injury, as an acute therapy to minimize, reduce, or limit brain injury and/or to improve recovery, reduce brain edema, or otherwise improve the patient's health.

The methods of treatment of mammals using a perispinal injector device to treat brain injury may utilize a variety of biologics, including, but not limited to biologic TNF antagonists; biologic antagonists of inflammatory interleukins, such as IL-1 (including, but not limited to, anakinra (Kineret®, (Biovitrum) and IL-1 Trap), IL-6, and IL-12 antagonists; IL-12 and IL-23 antagonists, including but not limited to ustekinumab (Stelara®); IL-17A antagonists, including but not limited to secukinumab (Cosentyx®) and ixekizumab (Taltz®); GM-CSF; erythropoietin (EPO); immune globulin (including intravenous immune globulin (IVIG, such as Gammagard®)); and other biologics. TNF antagonists used in the present invention include, but are not limited to, TNF receptor fusion proteins such as etanercept; chimeric TNF monoclonal antibodies (mAb) such as infliximab; fully human TNF mAbs such as adalimumab and golimumab; TNF mAb fragments, such as certolizumab pegol; domain TNF antibodies; anti-TNF nanobodies; humanized TNF mAbs or mAb fragments, etc. These methods include perispinal administration of a biologic, using a perispinal injection device, without direct intrathecal injection. Perispinal administration is defined as administration into the anatomic area within 10 cm of the spine. Perispinal administration, using a perispinal injection device, results in absorption into the cerebrospinal venous system (CSVS) (see Tobinick E. The cerebrospinal venous system: anatomy, physiology, and clinical implications. *Medscape General Medicine*, 8(1), 53f. (2006)). This invention, in several of its preferred embodiments, utilizes the CSVS to transport biologics to the brain and into the cerebrospinal fluid via retrograde venous flow, thereby bypassing the blood-brain barrier.

The vertebral venous system and a perispinal injection device can also be used to deliver other types of therapeutic agents to the bone marrow, cerebral cortex, eye, retina, cerebellum, brainstem, eighth cranial nerve, cochlea, inner ear, and cerebrospinal fluid.

Use of the vertebral venous system as a route to deliver therapeutic molecules administered by a perispinal injector device to the brain, bone marrow, retina, eye or auditory apparatus via retrograde venous flow is a novel delivery method for treating disorders of the brain, bone marrow, retina, eye or auditory apparatus.

This method allows the treatment of inflammatory or degenerative disorders of the retina and/or optic nerve, such as macular degeneration, diabetic retinopathy, glaucoma and retinitis pigmentosa, which involve excessive levels of TNF. Excess TNF appears to have a direct deleterious effect on vision, and etanercept, delivered via the vertebral venous system, appears to have the ability to ameliorate this adverse effect. Perispinal administration of these biologics enables the biologic to reach the internal contents of the eye, including the choroidal vasculature and the retina, in therapeutic amounts, via retrograde flow within the cranio-vertebral venous system.

As defined herein, the auditory apparatus includes the cochlea, the auditory division of the eighth cranial nerve, and the central auditory pathways. Sensorineural hearing loss is one particular category of hearing loss and is caused by lesions of the cochlea and/or the auditory division of the eighth cranial nerve. Prior to this invention, treatment of this condition was primarily limited to the use of hearing aids.

The present perispinal injection device may also be used with suitable medicines to treat neurodegenerative diseases, such as Parkinson's disease, Huntington's disease, Creutzfeld-Jacob disease, Alzheimer's disease, Frontotemporal dementia, Lewy Body disease, amyotrophic lateral sclerosis, etc.

Perispinal administration for delivery of neuroactive molecules other than etanercept, including biologics, cytokines, anti-cytokines, hormones or drugs via the vertebral venous system, in a manner similar to that outlined herein, may be performed. The neuroactive compounds include, but are not limited to: monoclonal antibodies to IL-17A or IL-23, such as guselkumab, tildrakizumab, MEDI2070 (AstraZeneca), secukinumab (Costentxy®&), ixekizumab (Taltz®), and ustekinumab (Stelara®); fusion proteins, such as etanercept (Enbrel®, Immunex); other TNF antagonists; erythropoietin (Epogen® (epoetin alpha) Amgen, Procrit® (epoetin alpha) Johnson & Johnson); G-CSF (Neupogen® (filgrastim), Amgen); GM-CSF; or other compounds with CNS, immune, or vascular therapeutic activity.

Perispinal Administration of Large and Small Molecules Using a Perispinal Injection Device are Embodiments of the Present Invention This invention involves the use of the above molecules delivered via the vertebral venous system either alone, as monotherapy, or combined with the use of other therapeutics delivered orally or otherwise for treatment of the conditions of consideration herein. For example, the inventor has demonstrated improvement in cognitive function in individuals with MCI or AD treated with either perispinal etanercept alone, or perispinal etanercept in combination with memantine and/or a cholinesterase inhibitor (chosen from the group of donepezil, rivastigmine or galantamine).

A biologic delivered via the vertebral venous system to the retina and the eye after perispinal administration is specifically included as part of the current invention.

The methods of the present invention are also distinguished from direct intrathecal administration of large molecules.

The large molecules of the current invention include, but are not limited to, the following:
  a. Colony-stimulating factors (including G-CSF, such as filgrastim, pegfilgrastim, and lenograstim; GM-CSF, including, but not limited to sargramostim and molgramostim; Erythroid growth factors, including, but not limited to: recombinant erythropoietin (EPO): epoetin alpha, darbepoetin alpha; and others.
  b. TNF antagonists with a molecular weight greater than or equal to 2,000 daltons, including, but not limited to: etanercept, infliximab, certolizumab pegol (Cimzia®), golimumab, adalimumab.
  c. Interferons, interferon antagonists, interferon fusion proteins, interleukins and interleukin antagonists, including, but not limited to: Interferon alfa-2a, rDNA [Interferon alfa-2a—Roferon A; Interferon, alpha-2a, recombinant]; Interferon alfa-2a, rDNA, PEG-[Peginterferon alfa-2a—Pegasys; interferon alpha-2a, recombinant, pegylated]; Interferon alfa-2b, rDNA [Interferon alfa-2—Intron A; Interferon, alpha-2b, recombinant]; Interferon alfa-2b, rDNA, PEG-[Peginterferon alfa-2b—PEG-Intron Powder; interferon alpha-2b, recombinant, pegylated]; Interferon alfa, rDNA/BioPartners [Interferon alpha, recombinant]; Interferon alfacon-1, rDNA [interferon alfacon-1—Infergen; consensus interferon, recombinant]; Interferon beta-1a, rDNA/Biogen [Interferon beta-1a-Avonex [recombinant]]; Interferon beta-1a, rDNA/Serono [Interferon beta-1a—Rebif [recombinant]]; Interferon betaser, rDNA/Berlex [Interferon beta-1b—Betaseron] (Betaseron has a MW of 18500 daltons); 2-166-Interferon beta1 (human fibroblast reduced), 17-L-serine-; interferon betaser, recombinant]; Interferon gamma, rDNA [Interferon gamma-1b—Actimmune; [recombinant]]; Interleukin-1ra, rDNA [Anakinra-Kineret; interleukin-1 receptor antagonist; IL-1i]; Interleukin-2, rDNA [Aldesleukin-Proleukin; des-alanyl-1, serine-125 interleukin-2, recombinant; IL-2]; Interleukin-2/diphtheria toxin, rDNA [Denileukin diftitox-ONTAK; interleukin-2 Fusion Protein; DAB389IL-2; interleukin-2/diphtheria toxin fusion protein, recombinant]; MRA (Roche, Chugai), a humanized anti-IL-6 receptor monoclonal antibody; Interleukin-2 receptor Mab, rDNA/Novartis [Basiliximab-Simulect; Interleukin-2 alpha receptor monoclonal antibody, recombinant]; Interleukin-2 receptor Mab, rDNA/Roche [Daclizumab-Zenapax; Interleukin-2 alpha receptor monoclonal antibody, recombinant]; Interleukin-11, rDNA [Oprelvekin-Neumega; des-Pro Interleukin-11, recombinant; des-Pro IL-11]; IL-6; IL-12; anti-IL-6; and anti-IL-12; monoclonal antibodies to IL-12, IL-17A, or IL-23, including, but not limited to guselkumab, tildrakizumab, MEDI2070 (AstraZeneca), secukinumab (Costentxy®), ixekizumab (Taltz®), and ustekinumab (Stelara®). As a general rule, interferons have molecular weights ranging from 15,000 to 21,000 daltons.
  d. Antibiotics with a molecular weight of 2.000 daltons or greater,
  e. Cancer therapeutics, with a molecular weight greater than or equal to 2,000, including those from the following classes:
    i. Monoclonal antibodies (mAb): including, but not limited to:
      1. Rituximab and rituximab biosimilar molecules;
      2. Epratuzumab.
      3. Alemtuzumab.
      4. Natalizumab.
    ii. Conjugates: Monoclonal antibody-drug, -toxin, or -radionuclide conjugates. These antibodies recognize specific antigenic determinants on malignant cells and their conjugates provide selective toxicity to those cells. A monoclonal antibody conjugate, for the purpose of this invention, is defined as a monoclonal antibody which is conjugated to either a drug, a toxin (such as diptheria toxin) or a radionuclide. These conjugates are particularly suited to perispinal administration, since they are extremely effective, even at low concentration, due to their biologic origin, and can be effectively delivered to the brain or to a brain tumor or lymphoma via the VVS by retrograde venous delivery into the brain. Therefore this class of therapeutic is effective for treating malignant tumors of the brain, either primary, such as glioblastoma multiforme, or metastatic, and for treating CNS lymphomas. These agents include yttrium-90 ibritummomab tiuxetan (Zevalin®) and iodine-131 tositumomab (Bexxar®) which are both murine mAbs against CD20 antigen that are conjugated to a radioactive source and thus selectively deliver radiation to tumors expressing the CD20 antigen (primarily expressed on B-lymphomas).

The above methods detailed for large molecules may be used identically for molecules with a MW of less than 2,000 daltons. The rationale for doing this is that many of these molecules, despite their smaller size, still have difficulty traversing the blood-brain barrier if administered systemically: or perispinal delivery without direct intrathecal injection results in more efficient delivery of these smaller molecules to the brain, the eye, the auditory apparatus or the bone marrow than does systemic or oral delivery. Perispinal administration and delivery to the brain, the eye, or other structures of the head thereby has the advantage of more efficient delivery across the BBB. Methotrexate and Amphotericin B have poor BBB penetration when given systemically, despite a MW of 454 and 924, respectively, and are often administered intrathecally for CNS use. The perispinal extrathecal methods of the present invention using perispinal injector devices are distinguished from direct intrathecal injection.

With respect to the small molecules of the present invention, they may be categorized as follows:
  1. Antibiotics: (Clinical use: treatment of bacterial infections of the central nervous system or the eye or the bone marrow utilizing perispinal injector device administration without direct intrathecal injection of the following): including, but not limited to cephalosporins, tetracyclines, macrolides, fluroquinolones.
  2. Antivirals: (Clinical use: treatment of viral infections of the bone marrow or the central nervous system, particularly meningitis or encephalitis utilizing perispinal injector device administration without direct intrathecal injection of the following): including, but not limited to oseltamivir, zanamivir, amantadine, anti-HIV drugs, anti-herpes drugs (including acyclovir, famciclovir, valacyclovir), anti-CMV drugs (cidofovir, foscarnet, ganciclovir) and ribavirin.
  3. Antifungal agents: (Clinical use: treatment of fungal infections of the central nervous system or the bone marrow utilizing perispinal injector device administration without direct intrathecal injection of the following): Amphotericin B and its congeners.
  4. Anti-parkinson drugs: (Clinical use: treatment of Parkinson's Disease utilizing perispinal administration without direct intrathecal injection of the following):

including, but not limited to levodopa, carbidopa, bromocriptine, selegiline, and dopamine.
5. Anti-psychotic agents: (Clinical use: treatment of psychoses, including schizophrenia, utilizing perispinal injector device administration without direct intrathecal injection of the following): haloperidol, Prolixin®, Moban®, Loxitane®, Serentil®, Trilafon®, Clozaril®, Geodon®, Risperdal®, Seroquel®, and Zyprexa®.
6. Antidepressants: (Clinical use: treatment of depression, including for acute depression as a substitute for electroconvulsive therapy), utilizing perispinal injector device administration without direct intrathecal injection of the following): including, but not limited to tricyclics, tetracyclics, trazadone, and SSRIs.
7. Anticonvulsants: (Clinical use: treatment of seizures, particularly status epilepticus, utilizing perispinal injector device administration without direct intrathecal injection of the following. In addition, please note that these antiepileptic drugs may also be used for treatment of other CNS disorders, such as psychoses and depression): including, but not limited to, Valium®, phenytoin, other hydantoins, barbiturates, gabapentin, lamotrigine, carbamazepine, topiramate, valproic acid, and zonisamide.
8. Opiates and opioids: (Clinical use: treatment of pain, including acute pain (e.g. labor and delivery, or field use following automobile accident, etc.; or chronic pain, as a substitute for chronic intrathecal drug delivery (e.g. as a substitute for chronic intrathecal morphine utilizing an implanted pump), or as a substitute for methadone maintenance treatment), utilizing perispinal injector device administration without direct intrathecal injection of the following): including, but not limited to morphine, oxycodone, other opiates and opioids, including oxycontin and methadone.

Bone Marrow Disorders

Perispinal injector devices can be used for enhanced delivery of therapeutic agents to the bone marrow. Compared with systemic administration, a perispinal injection device can deliver an enhanced concentration of a therapeutic agent to the bone marrow by direct retrograde delivery through the vertebral venous system (external vertebral venous plexus to internal vertebral venous plexus to basivertebral veins to bone marrow). Growth factors, including but not limited to, originator molecules and biosimilars of erythropoietin (Epogen® (epoetin alpha) Amgen, Procrit® (epoetin alpha) Johnson & Johnson); G-CSF (Neupogen® (filgrastim), Amgen); and GM-CSF can be delivered in this manner, as can other biologics, anti-cancer agents, antibiotics, gene therapy, cell therapeutics and anti-virals for treatment of bone marrow disorders, including, but not limited to, blood disorders, leukemia, lymphoma, genetic disorders, granulomatous disorders, infections (including osteomyelitis), aplastic anemia, and platelet disorders.

Otologic Disorders

As defined herein, the auditory apparatus includes the cochlea, the auditory division of the eighth cranial nerve, and the central auditory pathways. Sensorineural hearing loss is one particular category of hearing loss and is caused by lesions of the cochlea and/or the auditory division of the eighth cranial nerve. Prior to this invention, treatment of this condition was primarily limited to the use of hearing aids. The pathogenetic mechanism of most forms of hearing loss has yet to be fully defined. Hearing loss can be due to conductive problems, which is not the subject of this patent; central hearing loss due to lesions of the central auditory pathway; or sensorineural hearing loss.

Humans react to sounds that are transduced into neurally conducted impulses through the action of neuroepithelial cells (hair cells) and spiral ganglion cells (neurons) in the inner ear. These impulses are transmitted along the cochlear division of the eighth cranial nerve into the brainstem and the central auditory pathways. Presbycusis, or age-related hearing loss, is a type of sensorineural deafness which affects one-third of the population over the age of 75. The exact mechanism of presbycusis is unknown, and has long been thought to be multifactorial. Inflammation has not previously been thought to be a significant factor in the pathogenesis of presbycusis. Yet a previous study did suggest that genes encoded by the major histocompatibility complex (MHC) had a role in certain hearing disorders. (Bernstein, Acta Otolaryngol 1996 September; 116(5):666-71). The MHC is known to be central to the immune response and inflammation.

As will be discussed below there is now clinical evidence that inflammation has a role in the pathogenesis of various types of sensorineural hearing loss, including presbycusis. This opens up a new avenue of treatment of these disorders utilizing large molecules delivered by perispinal injector device administration without direct intrathecal injection, including biologic TNF inhibitors and other large molecules with a molecular weight equal to or greater than 2,000 daltons.

Preferred embodiments include, but are not limited to, the perispinal administration of TNF antagonists using a perispinal injector device for treatment of BI, including but not limited to chronic neurological dysfunction after stroke, including, but not limited to, ischemic stroke, hemorrhagic stroke, intraparenchymal hemorrhage, intraventricular hemorrhage, or stroke following subarachnoid hemorrhage. Preferred embodiments include but are not limited to the use of etanercept, infliximab, adalimumab, certolizumab pegol, and golimumab. Preferred embodiments include but are not limited to the use of TNF receptor fusion proteins, modified soluble TNF receptors, soluble TNF receptor constructs, TNF mAbs, humanized TNF mAbs, anti-TNF nanobodies (including, but not limited to, ATN-103 and PF-05230905, Ablynx and Pfizer), fully human TNF mAbs, chimeric TNF mAbs, domain TNF antibodies, mAB fragments, dominant negative TNF constructs (including, but not limited to Xpro 1595 (Xencor)), and TNF inhibitory single chain antibody fragments (including, but not limited to ESBA105); and biologic interleukin inhibitors, including, but not limited to, monoclonal antibodies to interleukin 17A, interleukin 12, or interleukin 23. Perispinal administration followed by Trendelenburg positioning, or by other forms of positioning of the body so that the head is maintained below horizontal following administration are additions to the preferred embodiments.

One preferred embodiment is the use of an autoinjector with an interspinous stop, as described herein, with the autoinjector containing a 27 gauge needle, designed to deliver 25 mg of etanercept in 2 ml of aqueous solution over 10 seconds after actuation when pressed to the skin overlying a cervical interspace (C6-7 or C7-T1 preferred), at a depth of 10 mm; followed by Trendelenburg positioning, to treat a patient with chronic post-stroke neurological dysfunction or a patient with chronic neurological dysfunction after traumatic brain injury.

Dosages and Routes of Administration

The therapeutically effective dosage of a biologic used for perispinal administration superficial to the ligamentum flavum using a perispinal injection device will in general be 10% to 100% of the dosage used as a single dose for systemic administration. The dosage used for systemic administration is known by those skilled in the art as it is specified in the FDA approved literature which accompanies each of these biologics. For example, if the usual dose when administered systemically is 50 mg, then the dose used for perispinal administration will usually be between 5 mg and 50 mg.

It will be appreciated by one of skill in the art that appropriate dosages of the compounds, and compositions comprising the compounds, can vary from patient to patient. The determination of the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Definitions provided herein are not intended alter the meanings commonly understood by one of skill in the art unless indicated otherwise. The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein. For all claims involving etanercept, this invention shall include use of the originator molecule (Enbrel®, Amgen/Immunex) and its biosimilars, including, but not limited to, SB4 (Samsung Bioepsis), brand name Benepali® or Brenzys®; GP2015 (Sandoz), brand name Erelzi®; Davictrel (HD203) (Hanwha Chemical); CHS-0214 (Coherus Biosciences), Etacept (Cipla); Intacept (Intas); Etanar/Yisaipu (Shanghai CP Guojian Pharmaceutical), etc.

REFERENCES

1. Tobinick E L. Targeted etanercept for discogenic neck pain: uncontrolled, open-label results in two adults. Clinical therapeutics. 2003; 25(4):1211-8.
2. Tobinick E L, Britschgi-Davoodifar S. Perispinal TNF-alpha inhibition for discogenic pain. Swiss Med Wkly. 2003; 133(11-12):170-7.
3. Tobinick E, Davoodifar S. Efficacy of etanercept delivered by perispinal administration for chronic back and/or neck disc-related pain: a study of clinical observations in 143 patients. Curr Med Res Opin. 2004; 20(7):1075-85.
4. Tobinick E L. Targeted etanercept for treatment-refractory pain due to bone metastasis: two case reports. Clinical therapeutics. 2003; 25(8):2279-88.
5. Tobinick E, inventor; TACT IP, LLC, assignee. U.S. Pat. No. 6,419,944, Cytokine Antagonists for the Treatment of Localized Disorders, filed Apr. 5, 2001. USA2001 Jul. 16, 2002.
6. Cohen S P, Bogduk N, Dragovich A, Buckenmaier C C, 3rd. Griffith S, Kurihara C, et al. Randomized, double-blind, placebo-controlled, dose-response, and preclinical safety study of transforaminal epidural etanercept for the treatment of sciatica. Anesthesiology. 2009; 110(5):1116-26.
7. Ohtori S, Miyagi M, Eguchi Y, Inoue G, Orita S, Ochiai N, et al. Epidural administration of spinal nerves with the tumor necrosis factor-alpha inhibitor, etanercept, compared with dexamethasone for treatment of sciatica in patients with lumbar spinal stenosis: a prospective randomized study. Spine. 2012; 37(6):439-44.
8. Freeman B J, Ludbrook G L, Hall S, Cousins M, Mitchell B, Jaros M. et al. Randomized, Double-blind, Placebo-Controlled, Trial of Transforaminal Epidural Etanercept for the Treatment of Symptomatic Lumbar Disc Herniation. Spine. 2013; 38(23):1986-94.
9. Winkelstein B A, Allen K D, Setton L A. Chapter 19: Intervertebral Disc Herniation: Pathophysiology and Emerging Therapies. In: Shapiro I M, Risbud M V, editors. The Intervertebral Disc. Wien, Austria: Springer-Verlag; 2014.
10. Sainoh T, Orita S, Miyagi M, Inoue G, Kamoda H, Ishikawa T, et al. Single Intradiscal Administration of the Tumor Necrosis Factor-Alpha Inhibitor, Etanercept, for Patients with Discogenic Low Back Pain. Pain medicine. 2016; 17:40-5.
11. Tobinick E, Gross H, Weinberger A, Cohen H. TNF-alpha modulation for treatment of Alzheimer's disease: a 6-month pilot study. MedGenMed. 2006; 8(2):25.
12. Tobinick E. Perispinal etanercept for treatment of Alzheimer's disease. Current Alzheimer research. 2007; 4(5):550-2.
13. Tobinick E L, Gross H. Rapid cognitive improvement in Alzheimer's disease following perispinal etanercept administration. Journal of neuroinflammation. 2008; 5:2.
14. Tobinick E L, Gross H. Rapid improvement in verbal fluency and aphasia following perispinal etanercept in Alzheimer's disease. BMC neurology. 2008; 8:27.
15. Tobinick E. Tumour necrosis factor modulation for treatment of Alzheimer's disease: rationale and current evidence. CNS drugs. 2009; 23(9):713-25.
16. Tobinick E. Perispinal etanercept: a new therapeutic paradigm in neurology. Expert review of neurotherapeutics. 2010; 10(6):985-1002.
17. Tobinick E. Perispinal etanercept produces rapid improvement in primary progressive aphasia: identification of a novel, rapidly reversible TNF-mediated pathophysiologic mechanism. Medscape journal of medicine. 2008; 10(6):135.
18. Tobinick E. Perispinal etanercept for neuroinflammatory disorders. Drug discovery today. 2009; 14(3-4):168-77.

19. Tobinick E. Deciphering the physiology underlying the rapid clinical effects of perispinal etanercept in Alzheimer's disease. Current Alzheimer research. 2012; 9(1):99-109.
20. Tobinick E. Rapid improvement of chronic stroke deficits after perispinal etanercept: three consecutive cases. CNS drugs. 2011; 25(2):145-55.
21. Tobinick E, Kim N M, Reyzin G, Rodriguez-Romanacce H, Depuy V. Selective TNF Inhibition for Chronic Stroke and Traumatic Brain Injury: An Observational Study Involving 629 Consecutive Patients Treated with Perispinal Etanercept. CNS drugs. 2012; 26(12):1051-70.
22. Tobinick E, Rodriguez-Romanacce H, Levine A, Ignatowski T A, Spengler R N. Immediate neurological recovery following perispinal etanercept years after brain injury. Clinical drug investigation. 2014; 34(5):361-6.
23. Ignatowski T A, Spengler R N, Dhandapani K M, Folkersma H, Butterworth R F, Tobinick E. Perispinal etanercept for post-stroke neurological and cognitive dysfunction: scientific rationale and current evidence. CNS drugs. 2014; 28(8):679-97.
24. Tobinick E L. Perispinal Delivery of CNS Drugs. CNS drugs. 2016; 30(6):469-80.
25. Louveau A, Smirnov I, Keyes T J, Eccles J D, Rouhani S J, Peske J D, et al. Structural and functional features of central nervous system lymphatic vessels. Nature. 2015; 523(7560):337-41.
26. Tobinick E L, Chen K, Chen X. Rapid intracerebroventricular delivery of Cu-DOTA-etanercept after peripheral administration demonstrated by PET imaging. BMC research notes. 2009; 2:28.
27. Steinberg G K, Kondziolka D, Wechsler L R, Lunsford L D, Coburn M L, Billigen J B, et al. Clinical Outcomes of Transplanted Modified Bone Marrow-Derived Mesenchymal Stem Cells in Stroke: A Phase 1/2a Study. Stroke. 2016; 47(7):1817-24.
28. Tobinick E. Perispinal etanercept: a new therapeutic paradigm in neurology. *Expert Review of Neurotherapeutics,* 10(6), 985-1002 (2010).
29. Tobinick E L, Chen K, Chen X. Rapid intracerebroventricular delivery of Cu-DOTA-etanercept after peripheral administration demonstrated by PET imaging. *BMC Res Notes,* 2, 28 (2009).
30. Breschet G. *Recherches anatomiques physiologiques et pathologiques sur le systáeme veineux* (Rouen fráeres, Paris, 1829).
31. Tobinick E L. Perispinal Delivery of CNS Drugs. *CNS Drugs.* 2016; 30(6):469-80.

The invention claimed is:

1. A perispinal injector device for injecting a fluid, comprising a medicine, between adjacent spinous processes of a patient, the perispinal injector device comprising:
a housing;
a syringe assembly that is slidably mounted within the housing;
wherein the syringe assembly comprises a needle;
an interspinous stop designed to facilitate positioning the needle over an interspinous space;
wherein the interspinous stop defines an aperture for deployment of the needle;
wherein the interspinous stop defines a bottom surface of the device for contacting skin;
wherein the interspinous stop has a side surface that is either flat or concave;
wherein the interspinous stop is configured to have the needle enter the skin in a region between the spinous processes of two adjacent vertebrae of the patient, when the bottom surface of the interspinous stop contacts the skin and the side surface of the interspinous stop is pressed against a spinal process of the patient.

2. The device of claim 1, wherein the side surface of the interspinous stop is concave.

3. The device of claim 1, a distance from a point on the side surface of the interspinous stop to a center of the aperture is less than 2 millimeters.

4. The device of claim 1, configured so that the needle, when deployed, extends beyond the bottom surface between 6 and 25 millimeters.

5. The device of claim 1, wherein the device is configured to store a volume between 1.5 and 10 milliliters of fluid within the housing.

6. The device of claim 1, wherein said side surface is concave, and a line segment, that passes through the aperture and has one end on said side surface and the other end on a surface of the interspinous stop that is opposite said side surface, has a length that is less than 4 millimeters.

7. The device of claim 1, further comprising an actuator for urging the syringe assembly to slide relative to the housing.

8. The device of claim 1, wherein said device defines at least one of an autoinjector and a pen injector.

9. A method of perispinal administration of a fluid containing a medicine, comprising:
contacting a bottom surface of an interspinous stop, designed to facilitate positioning a needle over an interspinous space, to skin of a patient;
pressing a flat or concave side surface of the interspinous stop against a spinal process of one vertebrae of the patient;
while the flat or concave side surface of the interspinous stop is pressed against the spinal process and the bottom surface is in contact with the skin, passing a tip of a needle through an aperture in the bottom surface of the interspinous stop and into the patient until the needle extends beyond the bottom surface between 6 and 25 millimeters, without hitting bone; and
while the tip of the needle is in the patient, injecting the fluid into the patient.

10. The method of claim 9 wherein the flat or concave side surface is concave.

11. The method of claim 9, wherein a rate at which the fluid is injected is between 4 and 10 seconds per cubic centimeter, and a volume of the fluid that is injected is between 1.5 and 4 milliliters.

12. The method of claim 9 wherein the medicine is selected from the group consisting of etanercept and etanercept biosimilars.

13. The method of claim 9 wherein the medicine comprises Xpro 1595.

14. A method of perispinal administration of a fluid containing a medicine using an interspinous stop to align a needle relative to a spinous process of one vertebrae of a patient, so that the needle enters the patient in a region between the spinous processes of two adjacent vertebrae of the patient, comprising:
pressing a flat or concave side surface of the interspinous stop against the spinal process of the one vertebrae while contacting a bottom surface of the interspinous stop to skin of the patient, so that an aperture in the bottom surface of the interspinous stop is in the region between the spinous processes of the two adjacent vertebrae of the patient;

moving the needle within the aperture in the interspinous stop so that a portion of the needle enters the patient, without hitting bone; and while pressing and contacting and the portion of the needle is within the patient without hitting bone, injecting, through the needle and into the patient, a volume of fluid containing the medicine.

15. The method of claim 14 wherein a rate at which the volume of fluid is injected is between 4 and 10 seconds per cubic centimeter.

16. The method of claim 14 wherein a viscosity of the volume of fluid is less than 100 centipoise at 20 degrees Centigrade.

17. The method of claim 14, comprising using an auto-injector to perform said injecting.

18. The method of claim 14 wherein the medicine is selected from the group consisting of etanercept and etanercept biosimilars.

19. The method of claim 14 wherein the medicine comprises Xpro 1595.

20. The method of claim 14, wherein the volume of fluid injected is between 1.5 and 4 milliliters.

21. The method of claim 14, wherein the side surface is flat.

22. The method of claim 14, wherein the side surface is concave.

23. The method of claim 14, wherein the tip of the needle extends beyond the bottom surface of the interspinous stop by between 6 and 25 millimeters while injecting the volume of fluid.

24. The method of claim 14, wherein the tip of the needle extends beyond the bottom surface of the interspinous stop, by a distance that places the tip of the needle superficial to the ligamentum flavum during said injecting.

25. The device of claim 14, a distance from a point on the side surface of the interspinous stop to a center of the aperture is less than 2 millimeters.

26. The device of claim 14, wherein said side surface is concave, and a line segment, that passes through the aperture and has one end on said side surface and the other end on a surface of the interspinous stop that is opposite said side surface, has a length that is less than 4 millimeters.

* * * * *